United States Patent
Yang et al.

(10) Patent No.: US 11,311,197 B2
(45) Date of Patent: Apr. 26, 2022

(54) PRODUCT, METHOD AND SYSTEM FOR MONITORING PHYSIOLOGICAL FUNCTION AND POSTURE

(75) Inventors: Chang-Ming Yang, Jhunan Township (TW); Tzu-Lin Yang, Jhunan Township (TW); Hao Yang, Taipei (TW)

(73) Assignee: MINGYOUNG BIOMEDICAL CORP., Miaoli (TW)

( * ) Notice: Subject to any disclaimer, the term of this patent is extended or adjusted under 35 U.S.C. 154(b) by 1232 days.

(21) Appl. No.: 13/401,711

(22) Filed: Feb. 21, 2012

(65) Prior Publication Data

US 2012/0215076 A1 Aug. 23, 2012

Related U.S. Application Data

(63) Continuation-in-part of application No. PCT/CN2010/001252, filed on Aug. 18, 2010, and a
(Continued)

(51) Int. Cl.
*A61B 5/00* (2006.01)
*A61B 5/0205* (2006.01)
(Continued)

(52) U.S. Cl.
CPC .......... *A61B 5/0205* (2013.01); *A61B 5/1116* (2013.01); *A61B 5/1126* (2013.01);
(Continued)

(58) Field of Classification Search
CPC ...... A61B 2562/029; A61B 2562/0219; A61B 2562/0271; A61B 5/6885; A61B 5/04085;
(Continued)

(56) References Cited

U.S. PATENT DOCUMENTS 4,988,981 A 1/1991 Zimmerman et al.
5,354,317 A 10/1994 Alt
(Continued)

FOREIGN PATENT DOCUMENTS

CN 1483380 A 3/2004
CN 1507833 A 6/2004
(Continued)

OTHER PUBLICATIONS

Yang et al.; "Sleeping ECG and body position monitoring system"; 31st Annual International Conference of the IEEE EMBS; Minneapolis, Minnesota; Sep. 2-6, 2009 (4 pages).
(Continued)

*Primary Examiner* — Shirley X Jian
(74) *Attorney, Agent, or Firm* — Chun-Ming Shih; HDLS IPR Services

(57) ABSTRACT

An article for detecting physiological function and posture status is disclosed. The article touches body directly or indirectly; wherein at least a group of non-posture physiological sensors are configured on this object and at least a switch, tension sensor, pressure sensor or pressure applicator are coupled with or touch this object; the switch, tension sensor, pressure sensor or pressure applicator are configured on a different or the same object with the physiological sensors, or divided into two parts that contact each other while external force applied; the non-posture physiological sensors sense the physiological function and posture status of the user.

20 Claims, 17 Drawing Sheets

Related U.S. Application Data continuation-in-part of application No. PCT/CN2009/000947, filed on Aug. 18, 2009.

(51) Int. Cl.
*A61B 5/11* (2006.01)
*A61B 5/282* (2021.01)

(52) U.S. Cl.
CPC .......... *A61B 5/282* (2021.01); *A61B 5/6805* (2013.01); *A61B 5/6885* (2013.01); *A61B 5/02055* (2013.01); *A61B 5/6891* (2013.01); *A61B 2562/029* (2013.01); *A61B 2562/0219* (2013.01); *A61B 2562/0271* (2013.01)

(58) Field of Classification Search
CPC ... A61B 5/1116; A61B 5/0205; A61B 5/6891; A61B 5/6805; A61B 5/02055; A61B 5/0402; A61B 5/0006; A61B 5/04012; A61B 5/0456; A61B 5/1118; A61B 5/681; A61B 5/021; A61B 5/02438; A61B 5/0408; A61B 5/742; A61B 5/1123; A61B 5/4812; A61B 5/6804; A61B 5/1126
See application file for complete search history.

(56) References Cited

U.S. PATENT DOCUMENTS

| | | | | |
|---|---|---|---|---|
| 5,469,861 A | | 11/1995 | Piscopo et al. | |
| 5,508,540 A | | 4/1996 | Ikeda et al. | |
| 5,865,760 A | * | 2/1999 | Lidman | A61N 1/36542 600/509 |
| 5,873,137 A | * | 2/1999 | Yavets-Chen | A61G 7/05776 5/188 |
| 5,914,701 A | | 6/1999 | Gersheneld et al. | |
| 6,210,771 B1 | * | 4/2001 | Post | H05K 3/10 428/100 |
| 6,384,729 B1 | | 5/2002 | Plotkin | |
| 6,930,608 B2 | | 8/2005 | Grajales et al. | |
| 7,502,643 B2 | | 3/2009 | Farringdon et al. | |
| 7,623,912 B2 | * | 11/2009 | Akselrod | A61B 5/02405 600/513 |
| 7,846,104 B2 | * | 12/2010 | MacQuarrie et al. | 600/481 |
| 8,374,688 B2 | * | 2/2013 | Libbus et al. | 600/547 |
| 8,388,530 B2 | * | 3/2013 | Shusterman | G06F 19/00 600/300 |
| 8,412,317 B2 | * | 4/2013 | Mazar | 600/547 |
| 8,668,653 B2 | * | 3/2014 | Nagata | A61B 5/0402 600/534 |
| 8,694,084 B2 | * | 4/2014 | Sullivan | A61B 5/04004 204/403.02 |
| 8,768,520 B2 | * | 7/2014 | Oexman | A47C 27/061 5/421 |
| 8,795,174 B2 | * | 8/2014 | Manicka et al. | 600/301 |
| 8,897,868 B2 | * | 11/2014 | Mazar et al. | 600/547 |
| 9,649,043 B2 | * | 5/2017 | Meftah | A61B 5/04011 |
| 2006/0122525 A1 | | 6/2006 | Shusterman | |
| 2006/0235315 A1 | * | 10/2006 | Akselrod | A61B 5/02405 600/509 |
| 2006/0235316 A1 | * | 10/2006 | Ungless | A61B 5/0006 600/509 |
| 2007/0049842 A1 | * | 3/2007 | Hill | A61B 5/08 600/534 |
| 2008/0052837 A1 | * | 3/2008 | Blumberg | A47C 23/002 5/727 |
| 2008/0064964 A1 | * | 3/2008 | Nagata | A61B 5/0402 600/484 |
| 2008/0230363 A1 | | 9/2008 | Yang et al. | |
| 2009/0069727 A1 | | 3/2009 | Neustaedter et al. | |
| 2009/0076336 A1 | * | 3/2009 | Mazar et al. | 600/300 |
| 2009/0076345 A1 | * | 3/2009 | Manicka et al. | 600/301 |
| 2009/0076410 A1 | * | 3/2009 | Libbus et al. | 600/547 |
| 2009/0156904 A1 | | 6/2009 | Shen | |
| 2009/0264792 A1 | * | 10/2009 | Mazar | 600/547 |
| 2009/0281394 A1 | * | 11/2009 | Russell et al. | 600/301 |
| 2010/0063365 A1 | * | 3/2010 | Pisani | A61B 5/0002 600/301 |
| 2010/0249628 A1 | * | 9/2010 | Kortelainen | A61B 5/1102 600/527 |
| 2010/0262026 A1 | * | 10/2010 | Meftah | A61B 5/04011 600/509 |
| 2011/0004110 A1 | * | 1/2011 | Shusterman | G06F 19/00 600/509 |
| 2011/0010014 A1 | * | 1/2011 | Oexman | A47C 27/061 700/276 |
| 2011/0043225 A1 | * | 2/2011 | Sullivan | A61B 5/04004 324/658 |
| 2011/0282164 A1 | * | 11/2011 | Yang et al. | 600/301 |
| 2013/0066168 A1 | * | 3/2013 | Yang et al. | 600/301 |
| 2013/0085347 A1 | * | 4/2013 | Manicka et al. | 600/301 |
| 2016/0287128 A1 | * | 10/2016 | Jain | A61B 5/6844 |

FOREIGN PATENT DOCUMENTS

| | | | |
|---|---|---|---|
| CN | 1618395 A | 5/2005 | |
| CN | 1961829 A | 5/2007 | |
| CN | 1985762 A | 6/2007 | |
| CN | 101053518 A | 10/2007 | |
| DE | 19927686 A1 | 3/2001 | |
| JP | 2009-18158 A | 1/2009 | |
| WO | 01/01855 A1 | 1/2001 | |
| WO | 03/105682 A1 | 12/2003 | |
| WO | 2007/033520 A1 | 3/2007 | |
| WO | WO 2008039082 A9 * | 4/2008 | A61B 5/0205 |
| WO | 2009/033361 A1 | 3/2009 | |
| WO | 2009/033362 A1 | 3/2009 | |
| WO | 2010/083630 A1 | 7/2010 | |

OTHER PUBLICATIONS

International Search Report dated Nov. 25, 2010, in corresponding International Patent Application No. PCT/CN2010/001252 (4 pages).
International Search Report dated May 20, 2010, in corresponding International Patent Application No. PCT/CN2009/000947 (3 pages).

\* cited by examiner lie on right  not press on the chest

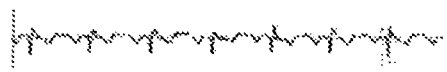

fig.6a lie on right  press on the left chest

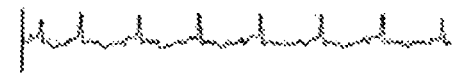

fig.6b lie on right  press on the right chest

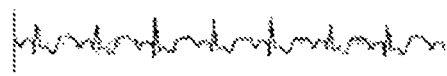

fig.6c lie on right  press on the left and right chest

fig.6d lie on left  not press on the chest

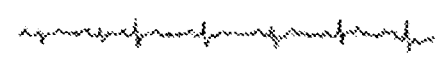

fig.6e lie on left  press on the left chest

fig.6f lie on left  press on the right chest

lie on left  press on the left and right chest

fig.6g fig.6h lie on back  not press on the chest

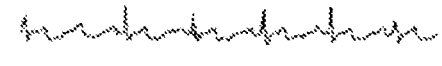

lie on back  press on the left chest

fig.6i fig.6j lie on back  press on the right chest

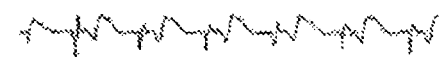

lie on back  press on the left and right chest

fig.6k fig.6L lie on back

fig.6m

| amplitude / phase | large | small |
|---|---|---|
| positive | lie on chest | lie on back |
| inverse | lie on left | lie on right |

PRODUCT, METHOD AND SYSTEM FOR MONITORING PHYSIOLOGICAL FUNCTION AND POSTURE

CROSS REFERENCES TO RELATED APPLICATIONS

This is a continuation-in-part application of PCT/CN2010/001252, filed on Aug. 18, 2010, which claims priority to PCT/CN2009/000947 filed on Aug. 18, 2009. The disclosures of these prior applications are incorporated by references in their entireties.

TECHNICAL FIELD

This disclosure relates to an object, a method and a system for detecting physiological function and posture status, which may be applied to areas such as physical training, medicine, fitness, health care, entertainment, industry security. In particular, it enables to learn the posture status of a user by sensing non-posture physiological signal and can be used to detect changes in terms of working safety, health condition, fitness results and posture status of a user.

BACKGROUND OF THE INVENTION

With the rapid improvement of living standard and health care, the human life expectancy is prolonging and proportion of aging population continues to increase. In such an "elderly society", issues of social welfare, medical technology and social security system arise accordingly, and a growing number of elders cannot be taken good care by their families. In addition, the change in lifestyle has led to a soaring proportion of people with chronic diseases such as hypertension, diabetes mellitus, gout, hyperlipaemia and heat diseases. As a result; a physiological function detection system is badly in need for them to detect physiological function at any time anywhere to prevent potential accidents.

For example, ECG is a most convenient and common tool for observing the heart, not only used in a physician's clinic for several minutes, but in many other occasions for long-term recording, i.e. Holter for 24 hours use. So what's an ideal ECG? It should be provided with comfortable electrode and can work continuously for long time without influence on people's daily life. Unfortunately, a patch electrode is most widely applied today, which may cause to feel uncomfortable on the skin for a long time; and thus is merely suitable for medical treatment on special occasions. For that reason, adoption of non-patch electrode to continuously obtain ECG signal has become an important research topic. One of current solutions is characterized by fixing the electrode and signal wires made of fabrics on clothes, chairs or beds to obtain ECG while the user will not feel uncomfortable; yet, the traditional electrocardiograph has so many wires preventing the user moving freely. In order to make the user comfortable when fixing signal wires on clothes, the signal wires should not be too long, many and complicated; but the reality is that electrodes and signal wires are needed as many as possible to obtain ECG for a user no matter what the posture is. To solve this dilemma, one way is to share signal wires by several electrodes and other physiological sensors.

On the other hand, due to high sensitivity to posture, ECG is varying all the time. It is known that when the user lies on his/her back and then arises, the heart rate will increase temporarily (reference to U.S. Pat. No. 5,354,317), that is, the ECG waveform change immediately when the position has changed (reference to U.S. Pat. No. 5,865,760). It is known that the ECG waveforms obtained by electrodes on different parts are not the same. Since the ECG is the result of periodic change from polarization to depolarization of myocardial cell membrane, while the change is projected on the "vector" formed by two electrodes, it is feasible theoretically to judge the body position via ECG. As disclosed in U.S. Pat. No. 7,502,643, numerous electrodes are taken to measured heartbeat, but not ECG waveform to detect the user's position. Position variation delivers important information in many aspects. For instance, when a person is changing his/her position frequently during sleeping, it may represent poor sleep quality; when a person is changing his/her position not as frequently as usual during sleeping, it may be thrombus blocking limbs or blood vessel of brain. U.S. Pat. Nos. 6,384,729 and 5,508,540 measure contraction of abdominal muscle using a sensor. U.S. Pat. No. 4,988,981 measures positions of hands and body using a sensor. U.S. Pat. No. 5,914,701 measures a position by the change in capacitance between two electrodes. U.S. Pat. No. 6,930,608 detects same physiological status using two sensors, but cannot detect the position unrelated to the original sensor. A patent JP2009-18158A reads physiological signal and the change in body position simultaneously by connecting a physiological sensor to a sensor (e.g. accelerometer, gyroscope and filter sensor) detecting position; such physiological sensor is not a pressure sensor or tension sensor and cannot filter noise. PCT/CN2005/001520 has discussed the connection of electronic switch with a physiological sensor to detect physiological signals, but not indicated it is feasible to detect the body position by the change in signals produced by the switch and physiological sensor too. None of the above-mentioned patents indicated that a signal wire may be shared by several sensors to prevent interruption of signals for recording by unnecessary physiological signal, and to reduce quantity and length of the signal wire consequently, while make the user more comfortable. Besides, when the user has changed his/her position, the physiological signal can still be obtained by the sensor subject to pressure.

Thus it can be seen obviously that the aforesaid object for detecting physiological function and posture status has inconvenience and defects with regard to structure and practical use. For this, there is a need for further improvement. To solve the above-mentioned problems, manufacturers have devoted a lot of energy to find a solution. However, for a long time, a suitable design has not been developed, and the ordinary products and methods do not posses the appropriate designs that can solve the above problems. Therefore, how to design a new type of object for detecting physiological function and posture status has become one of important research topics and the industry's goal for improvement.

SUMMARY OF THE INVENTION

An objective of the present invention is to overcome the disadvantages of current physiological function detection system and provide a new type of object for detecting physiological function and posture status; the know-how to be resolved is to detect the change of body position accurately to make it applicable.

Another objective of the present invention is to overcome the disadvantages of current physiological function detection method and provide a new method for detecting physiological function and posture status; the know-how to be resolved is to detect the change of body position accurately to make it applicable.

Further objective of the present invention is to overcome the disadvantages of current physiological function detection system and provide a new system for detecting physiological function and posture status; the know-how to be resolved is to detect the change of body position accurately to make it applicable.

The objectives and know-how of the present invention are accomplished by the technical solutions below: The object for detecting physiological function and posture status herein touches body directly or indirectly; wherein at least a group of non-posture physiological sensors are configured on this object and at least a switch, tension sensor, pressure sensor or a pressure applicator is coupled with or touches this object; the switch, tension sensor, pressure sensor or pressure applicator is configured on a different or the same object; the non-posture physiological sensor senses the physiological function and posture status of the user.

The objectives and know-how of the present invention can be further accomplished by technical solutions below:

Preferably, as for the object for detecting physiological function and posture status, the object that touches body directly or indirectly is at least one of clothes, underclothes, coat, bedspread, pillow, stockings, shoes, scarf, kerchief, gloves, apron, belt, closestool, carpet, floor map and chair.

Preferably, as for the object for detecting physiological function and posture status, wherein the non-posture physiological sensor is at least one of ECG, temperature, sweat, heartbeat, blood vessel meter, body fat analyzer, oxyhemoglobin saturation, respiration, brain wave, EMG, pulse, swallow, cough, sweating, speaking, blood pressure and blood sugar sensors.

Preferably, as for the object for detecting physiological function and posture status, wherein the non-posture physiological sensors are connected in series or parallel.

Preferably, as for the object for detecting physiological function and posture status, wherein the temperature sensor is positioned in materials of different thickness or thermal coefficient. The accuracy of judging posture is increased by means of the difference of heat conduction speed.

Preferably, as for the object for detecting physiological function and posture status, wherein at least one of the non-posture physiological sensors is a switch, tension sensor or pressure sensor at the same time.

Preferably, as for the object for detecting physiological function and posture status, wherein the physiological sensors are optionally connected in series or parallel with a resistor, an inductor or a capacitor.

Preferably, as for the object for detecting physiological function and posture status, wherein the a group of non-posture physiological sensors are of a different or the same type.

Preferably, as for the object for detecting physiological function and posture status, wherein the pressure sensor is a key switch.

Preferably, as for the object for detecting physiological function and posture status, wherein the tension sensor is a clip switch.

Preferably, as for the object for detecting physiological function and posture status, wherein a critical value of external force is set for every switch, tension sensor or pressure sensor.

The objectives and know-how of the present invention can be further accomplished by technical solutions below: The method for detecting physiological function and posture status, comprising: Configuring at least a group of non-posture physiological sensors on the object which touches body directly or indirectly, while connecting or touching a switch, tension sensor or pressure sensor; and sensing non-posture physiological signal by the physiological sensor so as to judge the posture of the user according to the non-posture physiological signal.

Preferably, as for the method for detecting physiological function and posture status, wherein the non-posture physiological signal further includes the signal acquired by the non-posture physiological sensor; it is to deduce deep/light sleep or consciousness by the changing of noise of the signal acquired by the non-posture physiological sensor.

Preferably, as for the method for detecting physiological function and posture status, wherein at least one of the non-posture physiological sensors is a switch sensor, a tension sensor or a pressure sensor at the same time which is used as a physiological sensor.

Preferably, as for the method for detecting physiological function and posture status, wherein the physiological sensor is coupled with a switch sensor, tension sensor or pressure sensor located differently.

Preferably, as for the method for detecting physiological function and posture status, wherein the physiological sensor is used for detecting physiological function of a man; the non-posture physiological sensor is at least one of ECG, temperature, sweat, heartbeat, blood vessel meter, body fat analyzer, oxyhemoglobin saturation, respiration, brain wave, EMG; pulse, speaking, blood pressure and blood sugar sensors.

Preferably, as for the method for detecting physiological function and posture status, wherein judging the posture of the user by the non-posture physiological signal further comprises: Generating characteristics of the physiological signal pursuant to the signal acquired by the non-posture physiological sensor and comparing with the posture database so as to judge the posture of the user.

Preferably, as for the method for detecting physiological function and posture status, wherein posture characteristics and parameters of judgment criteria are pre-stored in the database.

Preferably, as for the method for detecting physiological function and posture status, wherein posture characteristics and parameters of judgment criteria are optimized values made after considering the physiological signals of all users.

Preferably, as for the method for detecting physiological function and posture status, wherein generating characteristics of the physiological signal comprises: Finding out position and direction of at least one point of P, Q, R, S and T on ECG, as well as amplitudes of R, S and T, while reverse connecting at least one ECG electrode at front, back, right and left directions to produce inverse phase ECG.

Preferably, as for the method for detecting physiological function and posture status, wherein judging the posture of the user by the non-posture physiological signal further comprises: Generating ECG signal using two or three electrodes so as to detect change of the posture of the user.

Preferably, as for the method for detecting physiological function and posture status, wherein detecting change of the posture using a switch, tension sensor and pressure sensor coupled with the third electrode.

Preferably, as for the method for detecting physiological function and posture status, wherein generation of characteristics of the physiological signal features that, when judging sleeping position, the characteristics are numbered according to the following judgment criteria: Amplitude of T is k1 times the amplitude of R; whether or not there is P wave; whether or not R wave is positive; whether or not amplitude of R is k2 times the amplitude of S; whether or not there is positive S wave; whether or not there is negative S wave; whether or not there is positive T wave; whether or not amplitude of T is k3 times the amplitude of R; see below for the detail:

| | | VT > k1 * VR | P | +R | VR > k2 * VS | +S | −S | +T | VT > k3 * VR | 编码 Number |
|---|---|---|---|---|---|---|---|---|---|---|
| Lie on right side | Not press on the chest | | | | | 1 | | | | 08 |
| | Press on the right chest | | 1 | 1 | | | | 1 | | 62 |
| | Press on the left chest | | | 1 | | | | | | 20 |
| | Press on right and left chests | | | 1 | | | 1 | | | 24 |
| Lie on left side | Not press on the chest | | 1 | 1 | | | | 1 | 1 | 66 |
| | Press on the right chest | | 1 | 1 | 1 | | | 1 | 1 | 76 |
| | Press on the left chest | | 1 | | | 1 | | | | 48 |
| | Press on right and left chests | | 1 | 1 | | | 1 | 1 | 1 | 67 |
| Lie on back | Not press on the chest | | 1 | 1 | 1 | 1 | | 1 | | 7A |
| | Press on the right chest | | | | 1 | 1 | | | | 18 |
| | Press on the left chest | | 1 | 1 | 1 | | 1 | 1 | 1 | 77 |
| | Press on right and left chests | | | 1 | | | 1 | 1 | 1 | 27 |
| | Lie on stomach | 1 | | 1 | | | 1 | 1 | 1 | A7 |

Preferably, as for the method for detecting physiological function and posture status, wherein the k1 is from 0.6 to 1.0, k2 from 1.8 to 2.2, and k3 from 0.35 to 0.65.

Preferably, as for the method for detecting physiological function and posture status, wherein generation of characteristics of the physiological signal features that, when judging posture of a bicycle rider, the characteristics are numbered according to the following judgment criteria: Whether or not there is P wave; R wave is positive; whether or not there is T wave; see below for the detail:

| Position of electrode | Posture | P | +R | T |
|---|---|---|---|---|
| Jacket or trousers | Upper part of the body bends front | 1 | 1 | 1 |
| | Standing with erect upper part of the body | 0 | 1 | 0 |
| | Be seated on the bicycle with erect upper part of the body | 1 | 0 | 1 |
| Trousers and stockings | Standing | 0 | 1 | 1 |

Preferably, as for the method for detecting physiological function and posture status, wherein generation of characteristics of the physiological signal features that, when judging sleeping position by an electrode on the bed, the characteristics are numbered according to the following judgment criteria: Amplitude of S is k4 times the amplitude of R; whether amplitude of T is k5 times the amplitude of R; see below for the detail:

| | VS > 0.6 * VR | VT > 0.3 * VR |
|---|---|---|
| Lie on the back, neck not touch the bed and legs lift | 1 | 0 |
| Lie on the back, neck touches the bed and legs lift | 0 | 0 |
| Lie on the back, neck touches the bed and legs keep flat | 0 | 1 |

Preferably, as for the method for detecting physiological function and posture status, wherein the k4 is from 0.5 to 0.7, and k5 from 0.2 to 0.4.

Preferably, as for the method for detecting physiological function and posture status, wherein generation of characteristics of the physiological signal features that, when judging driving position, the characteristics are numbered according to the following judgment criteria: Amplitude of T is k6 times the amplitude of R.

Preferably, as for the method for detecting physiological function and posture status, wherein the k6 is from 0.7 to 0.9.

Preferably, as for the method for detecting physiological function and posture status, wherein posture characteristics and parameters of judgment criteria are pre-stored in the database; the parameters of judgment criteria are also determined by: Confirming whether or not the user is guided to pose specifically by using a posture sensor; the posture sensor is an accelerometer, gyroscope, fabric capacitance sensor or a video camera.

Preferably, as for the method for detecting physiological function and posture status, wherein generation of characteristics of the physiological signal features that, capturing the signal from the posture sensor at the same time; when the signal from the posture sensor is stronger than specific critical value, stopping analyzing physiological signal to prevent wrong judgment; the posture sensor is accelerometer, gyroscope, fabric capacitance sensor or video camera.

Preferably, as for the method for detecting physiological function and posture status, wherein the a group of non-posture physiological sensors are sensors of a different or the same type.

Preferably, as for the method for detecting physiological function and posture status, wherein the postures acquired form an actigraph.

The objectives and know-how of the present invention are accomplished by the technical solutions below: The system for detecting physiological function and posture status herein, comprising: at least a non-posture physiological sensor which is configured on the object touching body directly or indirectly; wherein the non-posture physiological sensor is coupled with or touches at least a switch, pressure or strain sensor; the switch, pressure or strain sensor or pressure applicator is configured on a different or the same object; the non-posture physiological sensor detects non-posture physiological signal; a signal processor, including a microcontroller used to process the signal acquired by the non-posture physiological sensor to judge posture of the user; signal wire is used to transmit the physiological signal.

Preferably, the system for detecting physiological function and posture status, further comprising: a wireless communication device sending a posture or digital physiological signal not processed by the microcontroller to personal information device, or the signal is transmitted to a person or organization faraway following personal information device's processing.

Preferably, the system for detecting physiological function and posture status, further comprising: an alarm device which will alarm when the characteristics of a physiological signal go beyond the range of characteristics of all physiological signals preset on the personal information device by the user.

Preferably, the system for detecting physiological function and posture status receives, records and displays physiological signals transmitted by one or several signal processors to form long-time and continuous personal physiological and position information.

Preferably, the system for detecting physiological function and posture status, wherein the posture information forms an actigraph.

Preferably, the system for detecting physiological function and posture status, comprising: It is to deduce deep/light sleep or consciousness by the changing of noise of the signal acquired by the non-posture physiological sensor.

Preferably, the system for detecting physiological function and posture status, wherein at least one of the non-posture physiological sensors is a switch sensor, tension sensor or pressure sensor at the same time which is used as a physiological sensor and placed in the object touching body.

Preferably, the system for detecting physiological function and posture status, wherein beside the signal wire, there is a reference area connected to the processor to detect leakage.

Preferably, the system for detecting physiological function and posture status, wherein near the physiological sensors, there is an air or a water filling device.

The present invention has obvious advantages and beneficial effects as compared with the prior art, and it has at least following advantages and beneficial effects in light of technical solutions described above.

It enables to detect the change in body position accurately.

Where there is a switch, pressure sensor or tension sensor connected, the sensor can be stopped to save electricity by automatic on/off, while it can be taken as a filter to reduce noise so that the action of the user can be detected for long term.

After the physiological sensor is coupled with a pressure sensor or tension sensor, noise can be filtered to prevent judging wrongly; the obtained physiological signal may weight with the result of the pressure sensor or tension sensor.

Something like a specific resistor or capacitor can be added between the physiological sensor and processor to cause signal enhancement or attenuation to produce different characteristics of physiological signals at different positions, which makes it easier to distinguish the user's body position and variation thereof.

Materials of different thickness or type can be set on a different or the same position of the object between the physiological sensor and body to obtain different rates of the physiological sensor so as to distinguish the user's body position.

It is able to detect leakage of fabrics.

Summarizing the above, the present invention can detect the change in body position accurately; it has significant improvement in terms of technology and renders more positive effects, representing a novel, advanced and practical new design.

The above description is only an overview of technical solutions provided by the present invention. In order to provide better understanding of technical means of the present invention to help users practice this invention, and in order to make the foregoing and other objectives, characteristics and advantages of the present invention more comprehensible, preferred embodiments, with accompanying drawings, are described in more details in the following:

BRIEF DESCRIPTION OF DRAWINGS

FIG. 6a-FIG. 6m illustrate ECG of various sleeping positions of the first preferred embodiment of the present invention.

Figure 1:
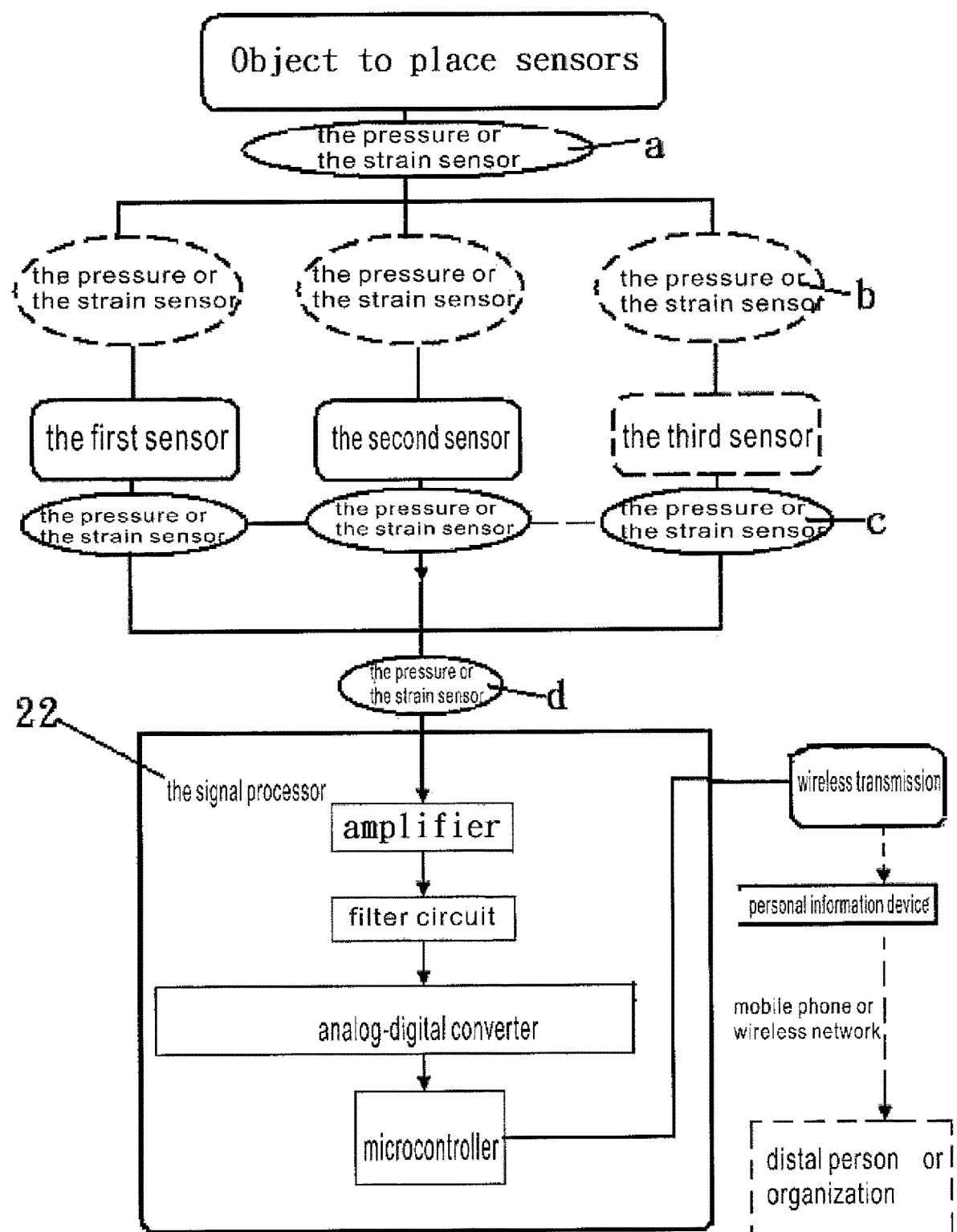
FIG. 1 illustrates the block diagram of the present invention.

--- a, b, c, d: Switch, pressure sensor or tension sensor
101, 102, 103, 104, 105, 106, 107, 108: Electrodes with key switches
10: Key switch
15: Electrode
12a, 12b, 12c, 12d, 12e: Electrodes
23: PDA or personal computer
120, 121, 122, 123, 124, 125, 126, 127: Electrodes
128, 129, 130, 131, 132, 133, 134, 135: Switches
12: PDA or personal computer
211, 212, 213, 214, 215, 216: Switches
22: Signal processor
17a, 17b, 17c, 17d: Electrodes

---

DETAILED DESCRIPTION

In order to further clarify the technical means adopted to achieve the anticipated objectives of the present invention as well as effects, the following details the ECG monitoring, as well as modes of application, structures, characteristics and effects of the method, device and system for judging body position by accompanying drawings and preferred embodiments.

With regard to the above explanation of this invention and other technological contents, special features and effectiveness, it will become clear from the following description using drawings and preferred embodiments. Through specific modes of application, one can further understand this invention in order to achieve the objectives with the technical means and effectiveness. However, the drawings provided are for reference and illustration only, and are not meant to limit the scope of this invention.

In the present invention, at least a group of non-posture physiological sensors are configured on this object that touches body directly or indirectly, which are coupled with at least a switch, tension sensor or pressure sensor; the at least a group of non-posture physiological sensors are used for sensing physiological signals from the original sensor alternately or simultaneously; when the physiological signals are processed and analyzed by digital signal processor, it is able to judge physiological function and body position of the user.

People will put on clothes, be seated on chairs or lie on the bed in most of the time, and most of the objects that contact human body for long term are made of textile or leather. Hence, sensors can be placed in hat, kerchief, shoes, clothes, chair, bedspread or pillow. In the present invention, a pressure sensor or tension sensor is coupled with the physiological sensor to reduce noise and start the next touching object automatically, while the previous object will be off automatically to save electricity, which means, it can realize long-time recording without constraining the user by the sensors and wires. Furthermore, the physiological signals can be obtained by sensors at different positions or different physiological signals obtained by sensors at same position, which can be acquired from the same or a different object to form long-term and continuous variation diagram of physiological function and body position, a great help for the health and safety of the user. Now, the technology is verified successfully on IEEE and EMBC Annual Conference 2009, and to be published in September, with title "Sleeping ECG and body position monitoring system".

The general block diagram of the present invention is as shown in FIG. 1. The object on which a physiological sensor is placed touches body directly or indirectly (e.g. the physiological sensor and skin are separated by underwear). A capacitor physiological sensor should be deployed on specific position with regard to special occasions and provided with a switch (e.g. a key switch or clip switch). The technology of the switch, or pressure sensor or tension sensor is disclosed by PCT/CN2005/001520 "Electronic device and method for using the same"; PCT/CN2008/001571 "Fabric able to form electronic element", PCT/CN2008/001570 "Cloth comprising separable sensitive areas", or PCT/CN2009/000118 "Sensing device", all of which are can serve as a switch, pressure sensor or tension sensor. FIG. 1 illustrates the connection thereof with a non-posture sensor; a, b, c and d are positions where the switch, or pressure sensor or tension sensor may be located. A pressure applicator may be a substitute with equal effects. That is to say, at least one of physiological sensors is coupled with at least a switch, pressure sensor, tension sensor or pressure applicator; alternatively, physiological sensors can contact with each other to enable the processor to receive physiological signals subject to external force, while, the physiological signals can be used for the judging the user's position variation. A critical value can be set to start the connected physiological sensors or close the object currently detected. In this sense, as a switch, it can be placed on an object and combined with a non-posture physiological sensor such as ECG electrode, thermistor, sweat electrode, brain wave electrode, EMG, respiration (impedance pneumography) sensor, heartbeat sensor, sweat sensor, body fat sensor, infrared thermometers, blood pressure sensor, pulse sensor, resistance-type respiration sensor, blood oxygen sensor and blood sugar sensor, so as to help judge the position accurately. Since a critical value of external force can be set for each switch, only when the external force exceeds the critical value, can the physiological signals enter the signal processor. Use of a switch aims to choose a proper part to capture physiological signal by considering the body position, eliminate the noise due to contact by mistake effectively and save electricity by powering off the previous object.

The physiological signal gets through the circuit of signal processor 22 via the first and second sensors, as well as switch, or pressure sensor or tension sensor connected thereto. The analog signal is firstly amplified by the amplifier; the analog band filter will be used for eliminating high and low frequency noises and performing analog-to-digital conversion, then signal will be analyzed by the program stored in the microcontroller which will compute characteristics of the signal and compare with that in the database, so as to judge the position of the user. Signal processor 22 has functions of display and alarming by sound and light. Meanwhile, a communication device with both wire and wireless transmission may be mounted in signal processor 22, through which, physiological and position signals can be sent to personal information devices (e.g. PDA or personal computer) which receive, take records of and display the physiological and position signals. Furthermore, the pre-processing (amplification, noise reduction by filter and analog-digital conversion of signals), analysis (extraction of signal characteristics) in signal processor 22, and storage of signals in database can be processed and stored in the personal information devices. For certain user, the personal information devices may receive one or several signals from signal processor 22. For example, when a group of sensors, a switch, a pressure sensor or a tension sensor and signal processor 22 is attached on the bed or chair of the user, it is able to form long-time and continuous personal physiological and position information without constraining the user by a traditional chip sensor and wires, and to alarm promptly as per the preset judgment criteria (e.g. the driver is not buckled up or catnaps).

In order to improve the touch between the sensor and body, something like resilient material, sponge, rubber, silicone rubber or spring, etc. may be added between the sensor and cloth or leather. The capacitive sensor (e.g. temperature sensor and sweat sensor) has a variable heat conductivity or moisture-penetrability due to different material or thickness. Moreover, a switch, pressure sensor or tension sensor may be added between the sensor and cloth or leather to prevent contact by mistake or transmit excess signals, the switch, pressure sensor or tension sensor can keep the starting of signal detection under control based on the pressure or strain. The disconnected sensor will consume no power, as a result in power saving.

The physiological signal has something to do with the switch, pressure or strain between the body and sensor. No signal will occur when there is no touch between the body and sensor; the signal quality will be inferior when the contact pressure between the body and sensor is not suitable.

In the present invention, the key switch or clip switch and sensor are connected in series or parallel. The physiological signal can only be transmitted to the circuit in case of sufficient pressure; thus, a signal wire may be shared by several sensors to prevent interruption of signals for recording by unnecessary physiological signal, and to reduce quantity and length of the signal wire consequently, while make the user more comfortable. Besides, when the user has changed his/her position, the physiological signal can still be obtained by the sensor subject to pressure. In one example, after a key switch connected with a sensor in series on the back, when the user lies on the bed, a physiological signal will be acquired by the sensor and transmitted to the circuit. In another example, after a clip switch connected with a sensor in parallel on the knee, the clip switch will be pulled as a result of strain when the user bends his/her knee, and the trousers will be forced to press close to the knee due to this strain. In this way, the sensor there will be able to acquire a physiological signal. When the user straightens legs, the loss of strain will cause the trousers not to press close to the knee; finally the sensor there will not be able to acquire a physiological signal. As shown in FIG. 1, when the sensor is connected to the physiological sensor, or pressure sensor or tension sensor using a signal wire, if the signal wire is not insulated there will leave a reference area connected to the processor near the signal wire so as to test leakage of the signal wire, e.g. the cloth is wet or the signal wire and the reference area contact to lead to short circuit. In case there is a circuit for treatment, or bare wire is a must for heating, temperature reduction, TENS (Transcutaneous Electrical Nerve Stimulation) or electrode, there will also be a reference area for test of leakage; alternatively, there may be a reference area near the lead on the cloth for the purpose of test of leakage in any time, which may be used as an electrode, a heater wire or an antenna.

Preferred Embodiment 1

Figure 2:
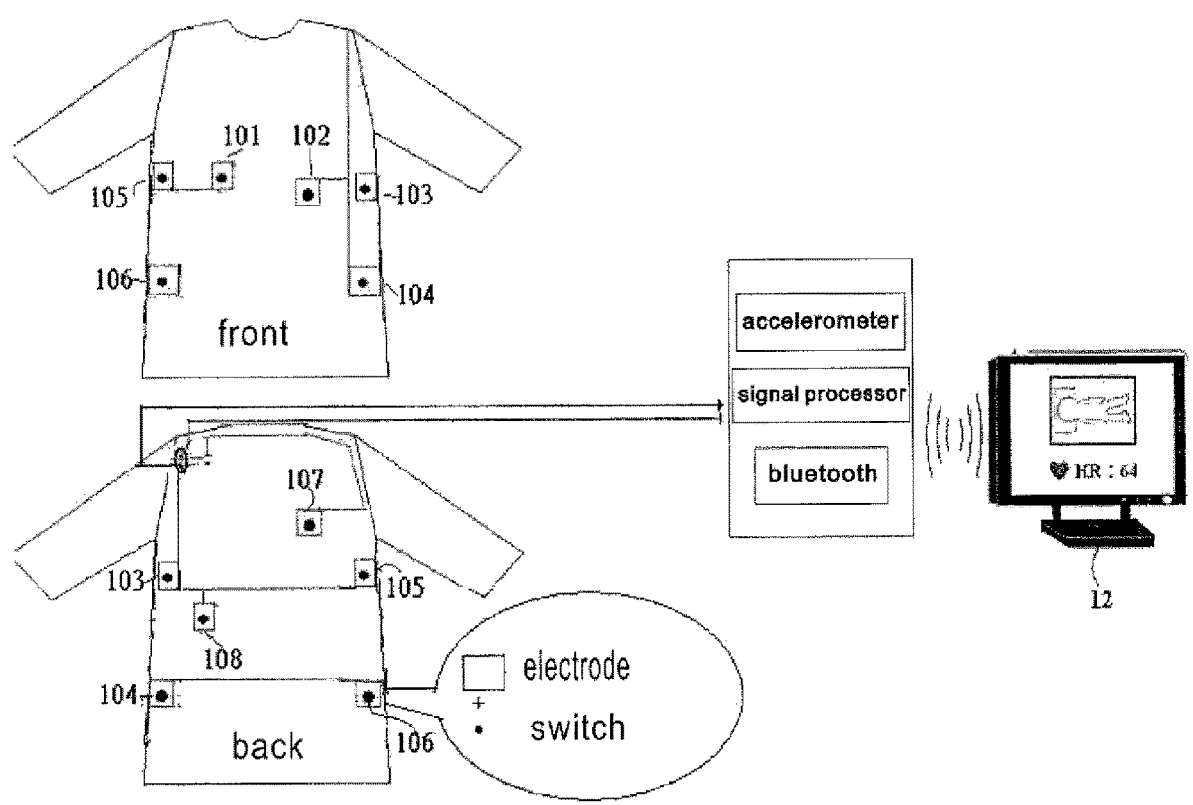
FIG. 2 illustrates the block diagram of the first preferred embodiment of the present invention when applied to pajamas.
Figure 3:
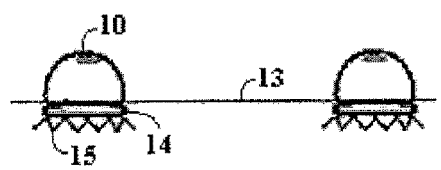
FIG. 3 illustrates structures of electrode and key switch of the first preferred embodiment of the present invention.

FIG. 2 and FIG. 3 illustrate separately the block diagram of the first preferred embodiment of the present invention when applied to pajamas, and structure diagram of electrode and key switch of the first preferred embodiment of the present invention. FIG. 2 is used for recording ECG and judging the body position, including electrodes 101, 102, 103, 104, 105, 106, 107 and 108 with key switches, signal processor 22, and PDA or personal computer 12. Structures of the electrodes and key switches are shown in FIG. 3. Electrode 15 that touches body is mounted on specific position on clothes 1; a key switch 10 is deployed above every electrode 15 connected with switch 10 in series. Once key switch 10 is pressed, it gets through and the physiological signal is connected to signal processor 22 which will amplify the analog physiological signal, filter to remove noise and perform analog-to-digital conversion before the ECG waveform is analyzed through the program; when key switch 10 is not pressed, it is disconnected and physiological signal cannot be connected to signal processor 22. For this reason, a different key switch 10 will be pressed for the user is changing sleeping position, so that physiological signals obtained by electrodes on different parts will be transmitted to instrument amplifier; of course the ECG waveform is varying accordingly; in this way, the body position may be judged according to the ECG waveform. As shown in FIG. 2, a signal wire is shared by several sensors to prevent interruption of signals for recording by unnecessary physiological signal. In this embodiment there are two signal wires and each is connected to four electrodes with switches, to reduce quantity and length of the signal wire consequently, while make the user more comfortable. Besides, when the user has changed his/her position, the physiological signal can still be obtained by the sensor subject to pressure.

The key switch as shown in FIG. 3 may be a multi-step key switch for producing different critical values; it may also be substituted by a pressure sensor or tension sensor and connected with a physiological sensor in series or parallel. The pressure sensor or tension sensor may be a digital or analog sensor. The switch, pressure sensor or tension sensor can be located on different cloth layers. The technology concerned is disclosed in early PCT/CN2008/001570 or PCT/CN2008/001571.

Figure 7A:
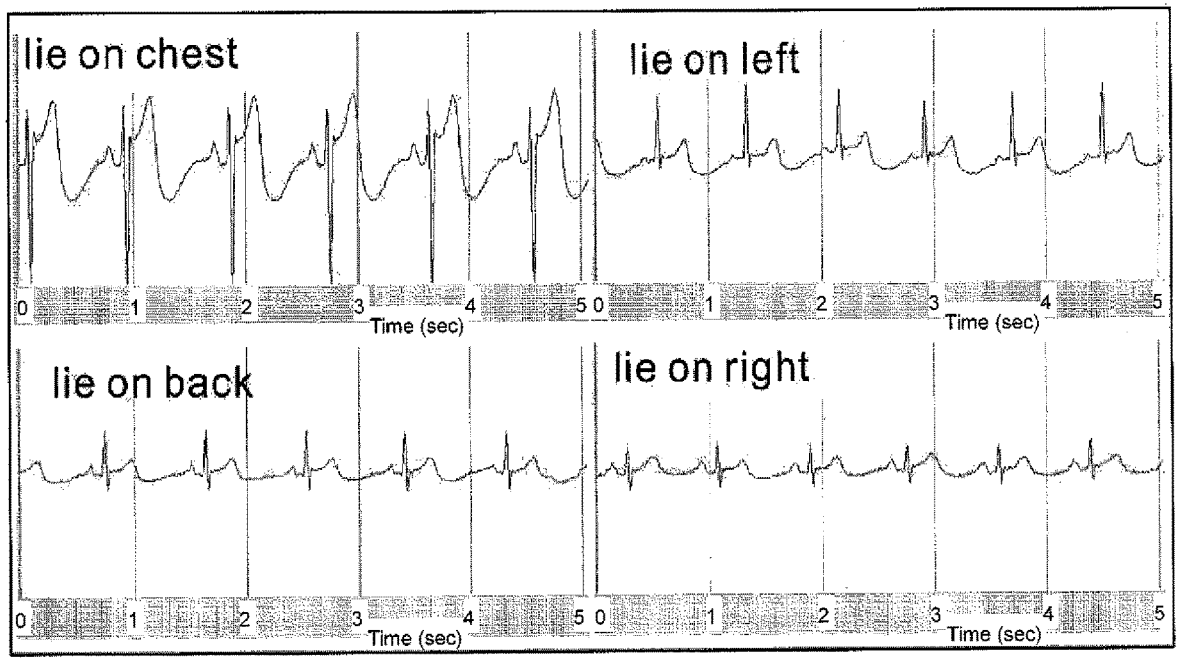
FIG. 7a-FIG. 7d illustrate ECG of four types of sleeping positions of the first preferred embodiment of the present invention.
Figure 7B:
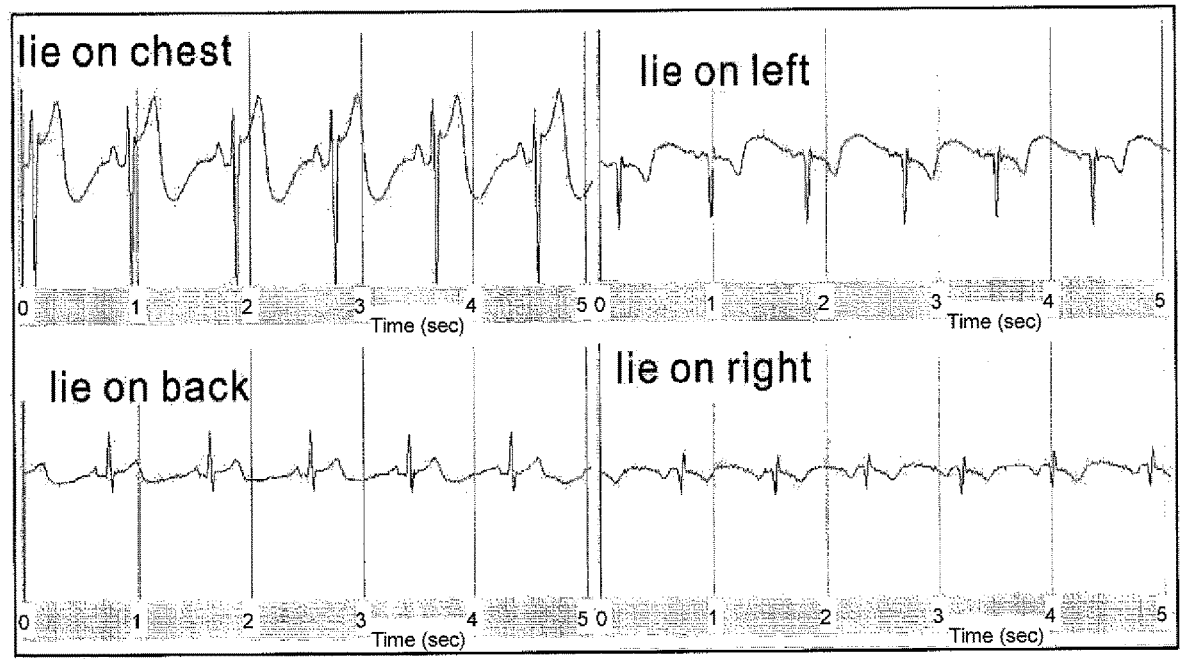
Figures 7C, 7D:
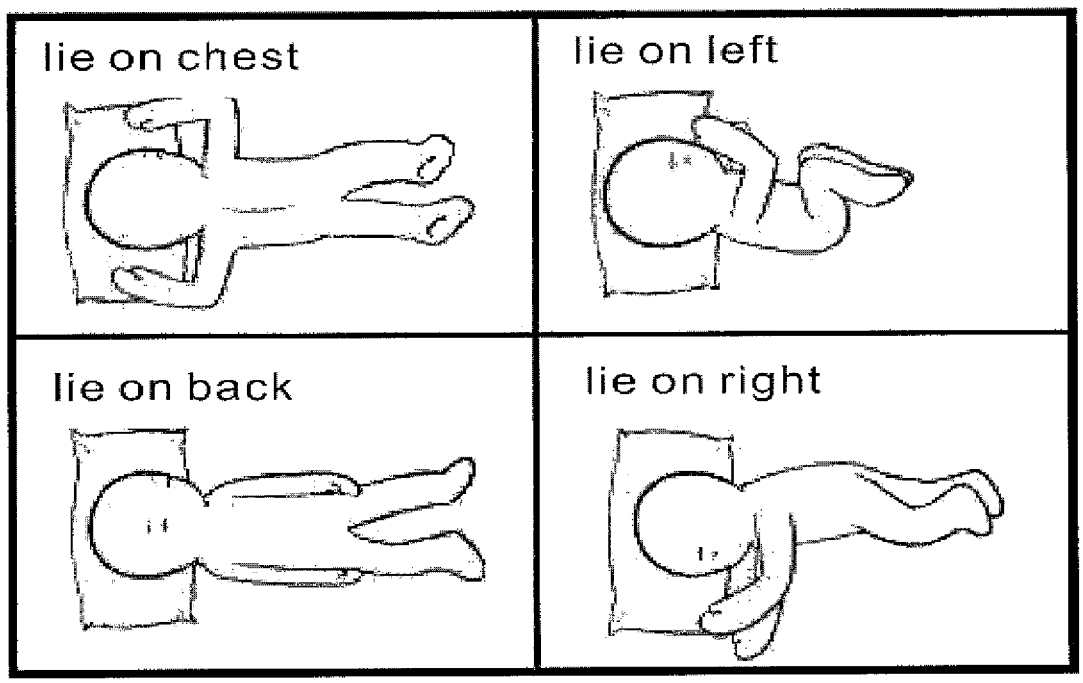

FIG. 7a illustrates ECG of four types of sleeping positions of the user. We can see that when the user lies on stomach, QRS (i.e. Q wave, R wave and S wave) waveform is the largest; when the user lies on back, it is the next; when the user lies on left, the waveform is sometimes similar to that when the user lies on back; when the user lies on right, the waveform is the smallest. Thus, we make reverse connection of electrode of ECG obtained when the user lies on right and left separately to cause inverse phase of the waveform outputted, as shown in FIG. 7b, which facilitates to learn the position of the user readily by ECG (as shown in FIG. 7c). The sleeping position of the user can be understood by ECG as shown in FIG. 7d. Similarly, in addition to physiological information, we can learn the change in the position of the user using the results of signals generated by a different physiological sensor, pressure sensor or tension sensor.

Thanks to electrodes on the clothes, a different electrode will be pressed when the user is changing sleeping position (e.g. lie on stomach, left and back) to result in different ECG waveform. The mechanism is as explained in the background. When the user lies on back and puts hands on chest, the electrode on chest will get through, yet the waveform obtained at this time is different from that when the user just lies on back or stomach. In this sense, it is feasible to detect the sleeping position and variation thereof by way of ECG waveform, while produce actigraph, through which, we can know whether the user is in deep or light sleep; alternatively, deep or light sleep can be deduced by heart rate variability or HRV obtained by ECG signal. In general, chest muscle contraction will bring about ECG baseline drift which is caused by respiration for a user in sleep. Thereby, it is able to obtain a respiration signal by capturing low frequency (lower than 0.3 Hz) signal of the ECG. If the user is in light sleep, the contact between the body and electrode is changing constantly, as a result in variation of ECG waveform. If so, the signal noise will increase. From this point, deep/light sleep and consciousness of the user can be deduced by the changing of the noise. Similarly, when the user is conscious, the noise will increase; only when the user is quiet or in sleep, the noise will decrease. Therefore, deep/light sleep and consciousness of the user can be deduced by the changing of the noise.

FIG. 6a-FIG. 6m illustrate ECG of various sleeping positions of the first preferred embodiment of the present invention. For most people, there are four types of sleeping position: Lie on back, lie on right, lie on left and lie on stomach. In order to obtain ECG in case of the four types of sleeping position, in the present invention, two electrodes are positioned around the pajamas, as shown in FIG. 2. As electrodes 101-108 include sponge 14 and key switch 10 features stereo structure, it increases the chance and reliability of contact between electrodes 101-108 and the body.

Besides, key switch 10 features stereo structure and the key is provided with a structure of electrode, which means the pressure sensor or tension sensor serves as an electrode at the same time. For instance, a switch or clip switch is virtually a kind of electrode. The technology is disclosed by PCT/CN2005/001520 "Electronic device and method for using the same"; PCT/CN2008/001571 "Fabric able to form electronic element", PCT/CN2008/001570 "Cloth comprising separable sensitive areas", or PCT/CN2009/000118 "Sensing device", therefore, the switch itself is an electrode and can be placed on an object as a physiological sensor such as ECG, EMG, respiration, impedance pneumography, heartbeat, sweat, EEG or body fat sensor. Alternatively, it may be the fact that a pressure sensor or tension sensor is connected with a physiological sensor. A critical value can be set to start the connected physiological sensor or close the object currently detected.

On the other hand, two pieces of conductive cloths form a capacitor, and the value of which is changing with the external pressure or strain. The mechanism is that a fixed frequency from external system is provided and the capacitance between two electrodes is detected. The changing of pressure or strain is embodied in the form of voltage or frequency. Thereby, the capacitor itself is a pressure sensor or tension sensor. When the body position has changed, the value of the capacitor will change accordingly. The physiological signal can only be received under a certain pressure; otherwise, the physiological signal will be cancelled. A critical value can be set to start the connected physiological sensor or close the object currently detected; two pieces of conductive cloths form a capacitor which can be considered as a switch. Meanwhile, as electrodes, the conductive cloths can be used physiological sensors.

In the same manner, the change of the value of capacitance between fabric (as an electrode) and the body may be measured using an oscillator (especially an astable oscillator), with equivalent effect. The change of the value of capacitance is embodied in the form of resonance frequency. In other words, as a pressure sensor, a piece of conductive cloth can be treated as a switch, an electrode and a physiological sensor for measuring ECG, EMG, impedance pneumography, heartbeat, sweat, EEG, body fat and so forth. The results obtained by two pieces of conductive cloths, and a piece of cloth and an astable oscillator will be same, one of which can be used as an electrode so as to measure ECG, respiration, EMG, brain wave or realize TENS and electroshock.

The purpose of choosing electrode distribution position is to obtain different solid angles (relative to heart), so that the projection of electric activity of the heart on vectors of electrodes 101-108 is various, which enables to judge the sleeping position. In view of the above-mentioned three types of sleeping position, the user's hands may put on chest or hold a toy or bedding to cause to start electrodes 101 and 102 on the chest. For this, four situations may happen for each of the three types of sleeping position. In want of body position variation in detail, it is able to deploy another electrode. After that, detailed results of body position variation will be obtained. In other words, more sensors, more accurately the position will be distinguished. When the user lies on stomach, his/her hands can hardly reach on the back to start electrodes 105 and 106, thus, it only needs to pay attention to electrodes 101 and 102. Please see Table 1 for various sleeping positions and electrodes 101-108 enabled. Various sleeping positions and enabled electrodes of the first preferred embodiment of the present invention are shown in Table 1.

TABLE 1

| | | Input end of ECG amplifier | | | | | | |
|---|---|---|---|---|---|---|---|---|
| | | Positive | | | | Negative | | |
| | | Electrode No. | | | | | | |
| | | 2 | 4 | 5 | 7 | 1 | 3 | 6 | 8 |
| Lie on right side | Not press on the chest | | | | + | | | | − |
| | Press on the right chest | | | | + | − | | | − |
| | Press on the left chest | + | | | + | | | | − |
| | Press on right and left chests | + | | | + | − | | | − |
| Lie on left side | Not press on the chest | | + | | | | | − | |
| | Press on the right chest | | + | | | − | − | | |
| | Press on the left chest | + | + | | | | | − | |
| | Press on right and left chests | + | + | | | − | − | | |
| Lie on back | Not press on the chest | | | + | | | | − | |
| | Press on the right chest | | | + | | − | − | | |
| | Press on the left chest | + | | + | | | | − | |
| | Press on right and left chests | + | | + | | − | − | | |
| | Lie on stomach | + | | | | − | | | |

Figure 4:
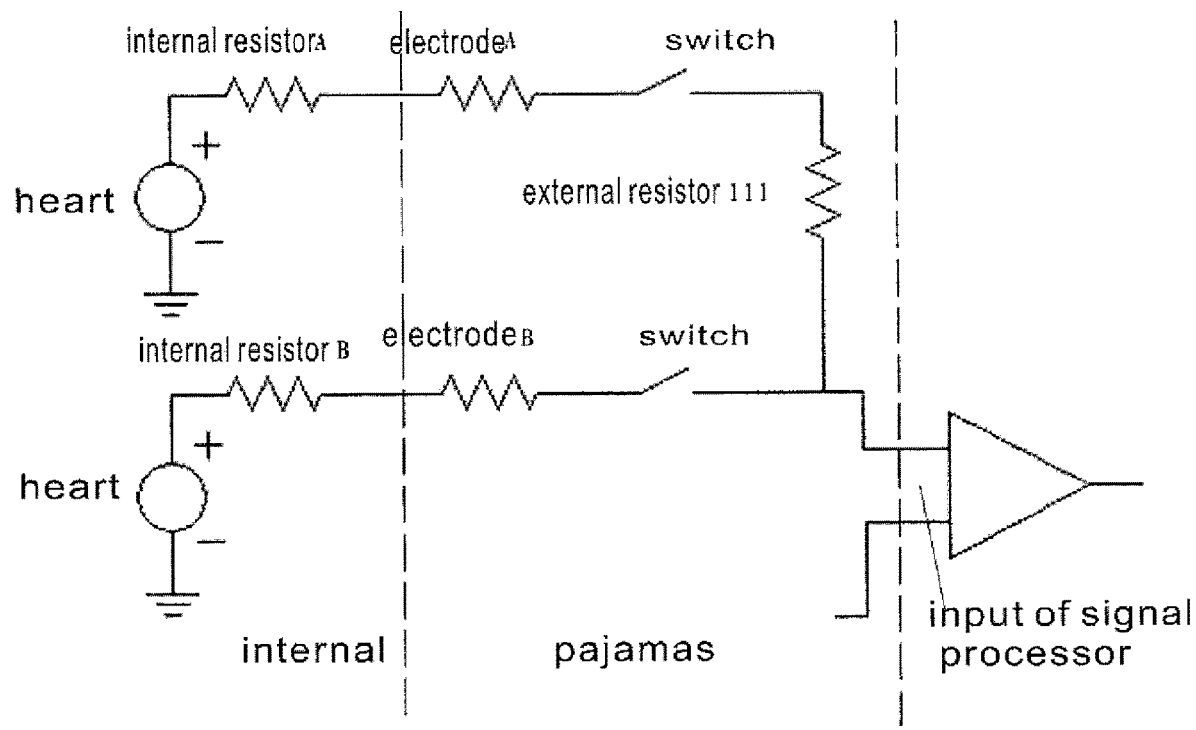
FIG. 4 illustrates equivalent circuits of internal resistance, electrode, external resistance, key switch and signal processor of the first preferred embodiment of the present invention.

From Table 1, two electrodes are connected in parallel and then to the input end of ECG amplifier, the equivalent circuits thereof are different from that of a traditional ECG (as shown in FIG. 4). It is possible that resistances for different parts of the body are varying greatly. For example, as the chest is next to the heart and the skin there is thin, the resistance for the chest is low, whereas the resistance for the back is much higher. Even if electrodes 101, 102, 105 and 106 are connected in parallel, the possibility is that enough effects cannot be achieved. In consideration of this, in one embodiment of the present invention, an extra resistor 111 is connected in series between signal processor 22 and some electrode to achieve better effects. In a similar way, a capacitor, resistor or an inductor may be optionally connected in series or parallel by considering the characteristics of body impedance and signal frequency (different frequency for EMG, capacity of blood vessel, respiration, sweat, blood oxygen, body temperature, body fat and so forth).

Figure 5:
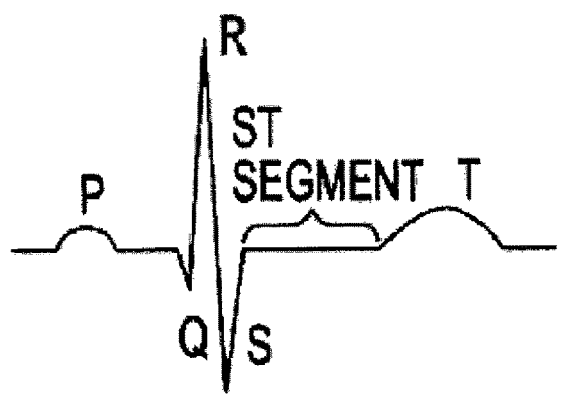
FIG. 5 illustrates definition diagram of every point of ECG of the first preferred embodiment of the present invention.
Figure 8:
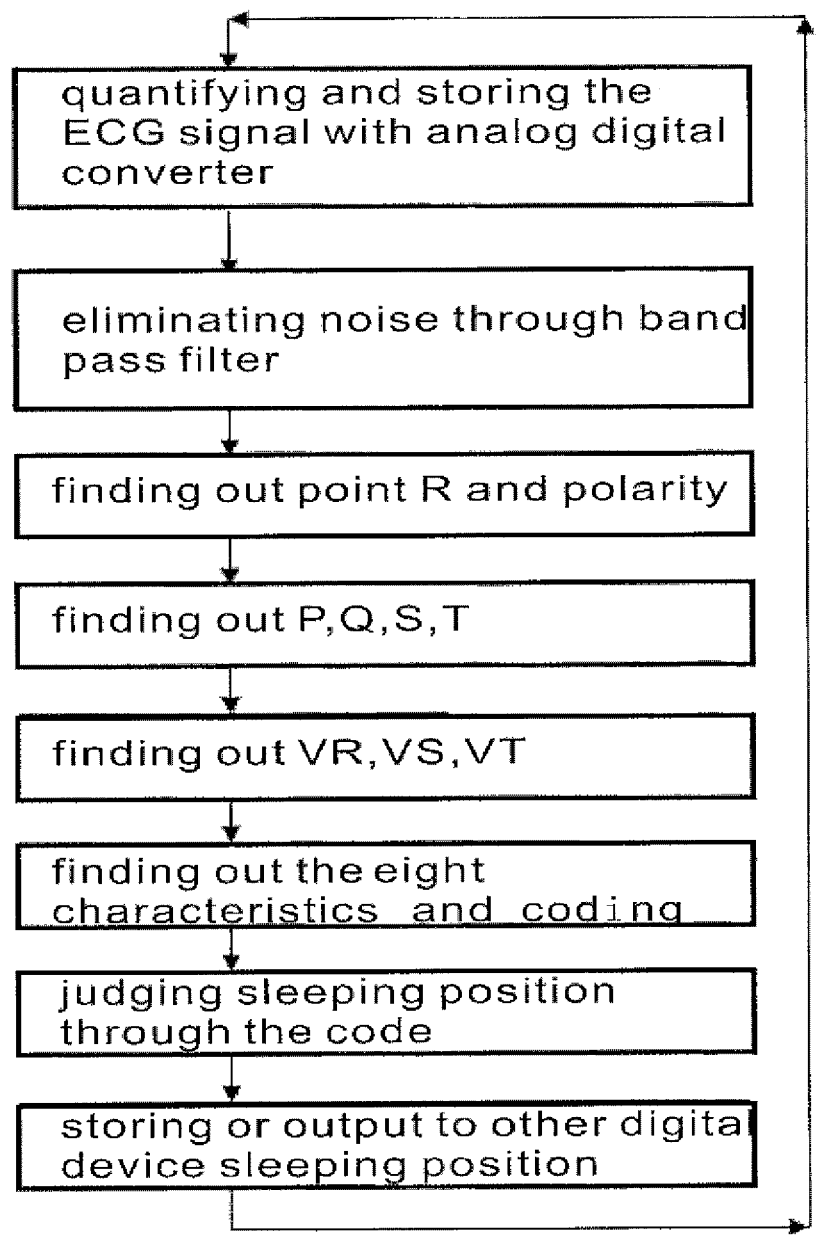
FIG. 8 illustrates the flow diagram of judging position by ECG signal of the first preferred embodiment of the present invention.

As shown in FIG. 5 is the definition of every point of typical Lead I ECG. The algorithm adopted for analyzing ECG waveform by the program stored in the microcontroller or remote control device is as follows: Firstly processing the ECG signal in signal processor 22 using the prior digital signal technology (see Biomedical Digital Signal Process, by Willis J. Tompkins, 1993). As shown in FIG. 8, in the first embodiment of the present invention, the method of processing the ECG signal is as below: Firstly quantifying and storing the ECG signal with analog-digital converter in signal processor 22; eliminating noise through band filter (four-order Bessel band filter, 0.06-40 Hz); finding out point R (take point with largest amplitude) of ECG signal and polarity by means of program, as well as points P, Q, S and T. Since the electrode position is not as usual the 12-lead standard position, the waveform is different from standard waveform, as shown in FIG. 5. However, those skilled in the art can still find out the points as per the characteristics of R, P, Q, S and T, as well as amplitudes of R, S and T (defined as VR, VS, VT). For some sleeping position, the ECG features no P, S or T wave (but R peak) or direction thereof is contrary to lead I, which thus can be considered as characteristics for judging certain sleeping position. The present invention concludes eight characteristics after analysis on various sleeping positions, in line with the judgment criteria, mark 1, otherwise 0, see below:

1. Amplitude of T wave is k1 times that of R wave: This will happen only when the user lies on stomach, mark VT>k1*VR, wherein k1 is from 0.6-1.0, preferably 0.8;
2. P wave: No matter the direction is positive or negative, mark P;
3. Polarity of R wave: 1 for positive, mark +R;
4. Amplitude of R waveform is twice that of S waveform: If there is remarkable R wave, mark 1 and VR>k2*VS, wherein k2 is from 1.8-2.2, preferably 2;
5. Positive S wave: 1 for positive, mark +S;
6. Negative S wave: 1 for negative, mark −S;
7. Positive T wave: 1 for positive, mark +T;
8. Amplitude of T wave is k2 times that of R wave: Mark VT>k3*VR, wherein k3 is from 0.35-0.65, preferably 0.5;

As shown in FIG. 6 is ECG signals for typical sleeping positions.

See Table 2 for the conclusion of characteristics of various sleeping positions. If one of such characteristics occurs, mark 1. In the present invention, the eight characteristics are orderly numbered in one byte and expressed by two digits based on hex.

FIG. 7a shows the ECG results of FIG. 2. Every pair of electrodes are coupled with a pressure sensor separately and outputted to a processor. We can find that when the user lies on stomach, amplitudes of Q, R and S are highest; when the user lies on back and left, amplitudes of Q, R and S are medium; when the user lies on left, P wave is not distinct; when the user lies on right, amplitudes of Q, R and S are lowest, yet P wave is distinct.

As shown in FIG. 7b, the electrodes on right and left are reverse connected to the nodes of the processor to produce inverse phase ECG, which enables to distinguish the variation of ECG when the user lies on back and left. The ECG has inverse phase when the user lies on left and right, based on which, analysis logic can be summed up as in FIG. 7c: When the amplitude is large and positive, the user lies on stomach; when the amplitude is large and negative, the user lies on left; when the amplitude is small and positive, the user lies on back. Based on this analysis, the position of the user can be learnt as shown in FIG. 7d.

TABLE 2

| | | VT > k1 * VR | P | +R | VR > k2 * VS | +S | −S | +T | VT > k3 * VR | Number |
|---|---|---|---|---|---|---|---|---|---|---|
| Lie on right side | Not press on the chest | | | | | | 1 | | | 08 |
| | Press on the right chest | | 1 | 1 | | | | 1 | | 62 |
| | Press on the left chest | | | | | 1 | | | | 20 |

TABLE 2-continued

| | | VT > k1 * VR | P | +R | VR > k2 * VS | +S | −S | +T | VT > k3 * VR | Number |
|---|---|---|---|---|---|---|---|---|---|---|
| | Press on right and left chests | | | 1 | | 1 | | | | 24 |
| Lie on left side | Not press on the chest | | 1 | 1 | | | 1 | 1 | | 66 |
| | Press on the right chest | | 1 | 1 | 1 | | 1 | 1 | | 76 |
| | Press on the left chest | | 1 | | | 1 | | | | 48 |
| | Press on right and left chests | | 1 | 1 | | | 1 | 1 | 1 | 67 |
| Lie on back | Not press on the chest | | 1 | 1 | 1 | 1 | | 1 | | 7A |
| | Press on the right chest | | | | 1 | 1 | | | | 18 |
| | Press on the left chest | | 1 | 1 | 1 | | 1 | 1 | 1 | 77 |
| | Press on right and left chests | | | 1 | | | 1 | 1 | 1 | 27 |
| Lie on stomach | | 1 | | 1 | | | 1 | 1 | 1 | A7 |

In practical application, ECG signal for every user may be different somewhat. For different users, in order to achieve better effect, values of k1-k3 should be made differently. For this reason, on the circuit board of signal processor 22 of the present invention is configured an accelerometer, gyroscope sensor, tilter sensor or geomagnetometer. When it is static, it is able to know the angle of inclination between the accelerometer or other position sensors and the ground. For starting the system for the first time, the user will be prompted to fix signal processor 22 on shoulders manually to determine the sleeping position of the user. The user can change the sleeping position constantly, which will be analyzed by the system. Similarly, the present invention may make use of other types of sensors to detect a position, such as gyroscope, video camera and so forth. The system enables a function of setting parameters by self-learning. When the user makes various sleeping positions, the system will extract characteristics of points R, P, Q, S and T with regard to the waveform of ECG signal for every kind of position while calculating values of k1-k3. The average or weighted value of the result will be taken as the setting value of the parameter in practice to adjust the judgment criteria optimally for the user, see FIG. 8 for flow chart. Alternatively, the user may be required to change sleeping position variously without an accelerometer or other position sensors so that the system can analyze ECG signal for every kind of sleeping position. In practical use, since pajamas are loose, the accelerometer is unable to press against the body closely to deliver various sleeping positions to the system. For this, the present invention further discloses another method: Prompting the user to make certain sleeping position as requested when the system is setting parameters by self-learning to enable the system to determine values of k1-k3. Besides, more electrode sensors are available on different places, more diverse positions may be obtained. Especially, more satisfactory results can be obtained by adjusting the critical value of a different switch, pressure sensor or tension sensor to adapt to different figures and weights.

Preferred Embodiment 2

Figure 9A:
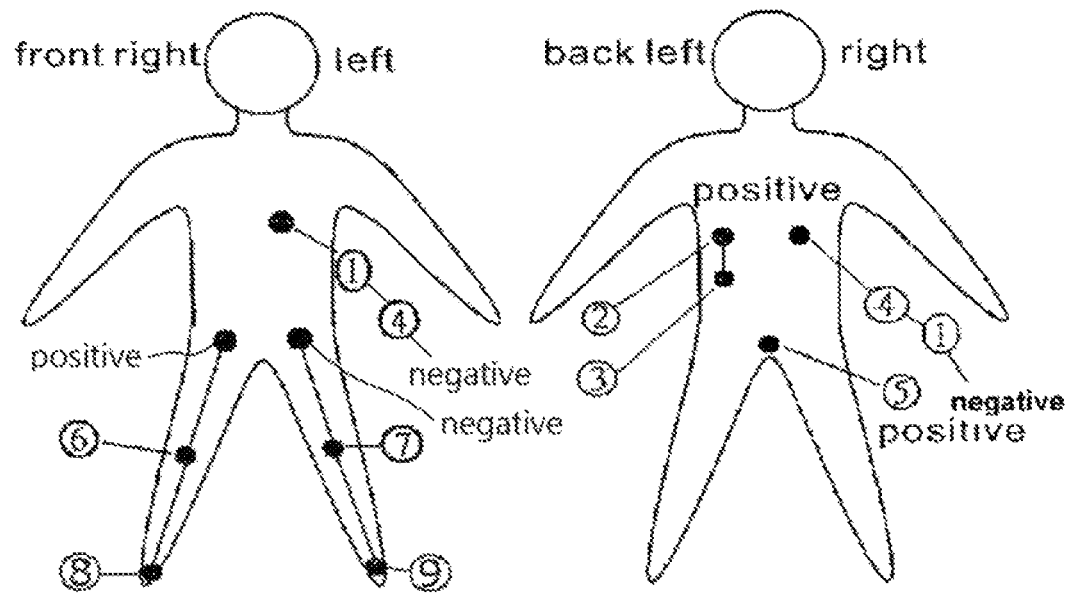
FIG. 9a-FIG. 9d illustrate the electrode position and connection diagram of the second preferred embodiment of the present invention when applied to a bicycle rider's coat and trousers.

FIG. 9a illustrates the electrode position and connection diagram of the second preferred embodiment of the present invention when applied to a bicycle rider's coat and trousers. The section of circuits may be referred to embodiment 1; wherein electrodes 1-5 are connected in series to a key switch or pressure sensor separately.

Figure 9B:
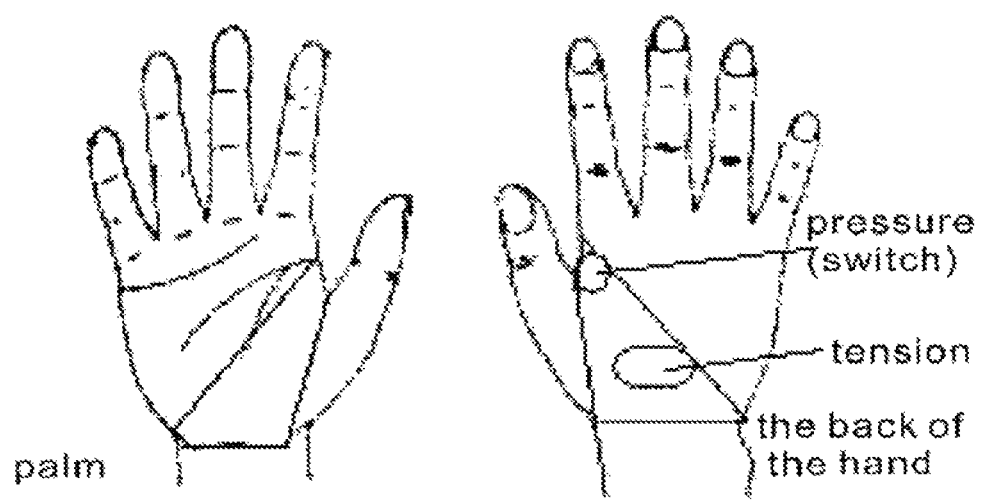

FIG. 9b illustrates the switch, pressure or strain at the gloves. Both right and left hands are with conductive cloth which are made of elastic materials and coupled with a switch, pressure sensor or tension sensor. When walking or sitting, the CEG signals for right and left hands will be sent to the processor to form bipolar ECG. Additionally, a three electrode ECG will be obtained if there is conductive cloth on the hem near the ass, which directly touches the ass, or if some conductive material on underpants touches with the pressure sensor or switch on the hem. The three electrode ECG gives lead two ECG.

Figure 9C:
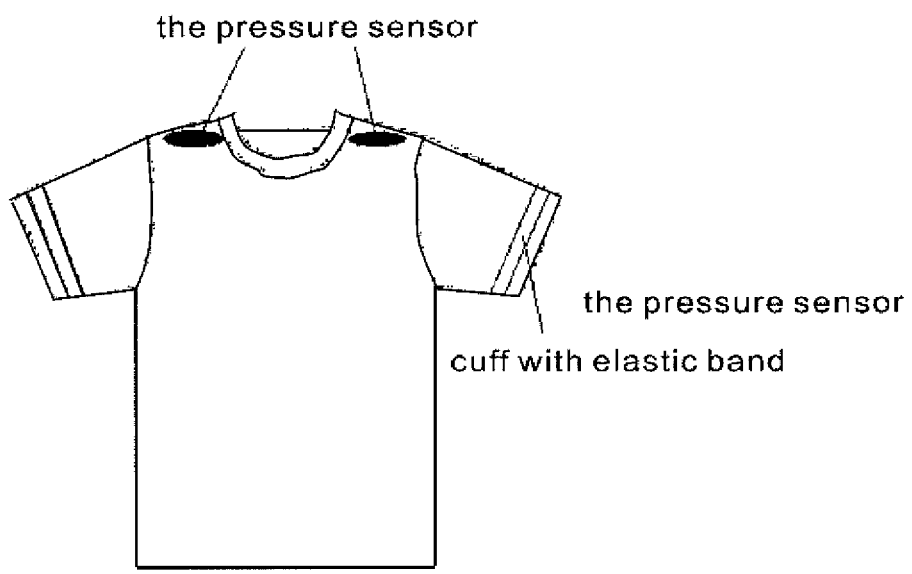
Figure 9D:
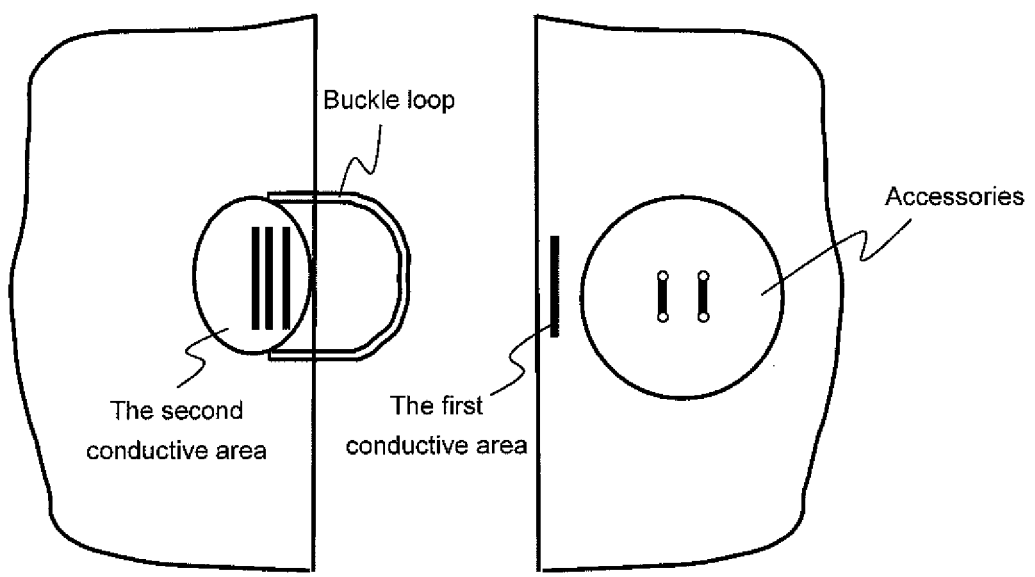

If in summer, the gloves will be made of resilient materials like rubber band or fixed on the cuffs of the shirt, instead of FIG. 9c, to make the cuffs touch the skin despite moving. Meanwhile, there is conductive cloth on the cuffs. A pressure sensor or tension sensor (as shown in FIG. 9d) can be connected to the conductive cloth so as to measure the touch between the cuffs and arms. Wherein in the first conductive area there is a button structure, and an elastic buckle loop (component 3 as shown in FIG. 9d) in the second conductive area to fasten the button. The second conductive area may be divided into three sections of conductive area. Due to different strain, it will contact with different conductive area, which requires number and position differently; in this way, it is able to measure the strains of the first and second conductive areas using a capacitor or resistor; and the first and second conductive areas can serve as electrodes for sensing ECG or EMG, or are connected to other non-posture physiological sensors for detecting physiological signals. The tension sensor may also be configured on other parts of the coat, e.g. on the hem of the coat or opening of trousers, or the joint of the coat and trousers, the trousers and stockings. With this structure, it is able to detect sweat, respiration, body fat, brain wave or facilitate TENS too. In addition, there may be a pressure sensor connected to the electrode fabric below and signal processor on left or right shoulder. When the signal processor is placed one shoulder, ECG detection will be started correspondingly. Something like shoulder pads may also be put on right or left shoulder to make the pressure sensor get through and send ECG signal by the electrodes. In order to realize detection for long time, a control box or the like may be used to hold the electrode fabric to prevent it becoming apart from the body. The pressure sensor may be substituted by a tension sensor or switch sensor, that is, the signal will be more stable after testing the pressure or strain between the electrode fabric and body with a tension sensor or pressure sensor.

Figure 10A:
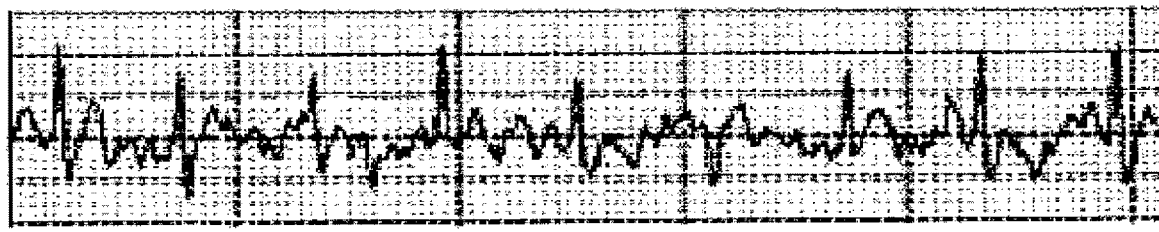
FIG. 10a-FIG. 10d illustrate ECG of various positions of the second preferred embodiment of the present invention.
Figure 10B:
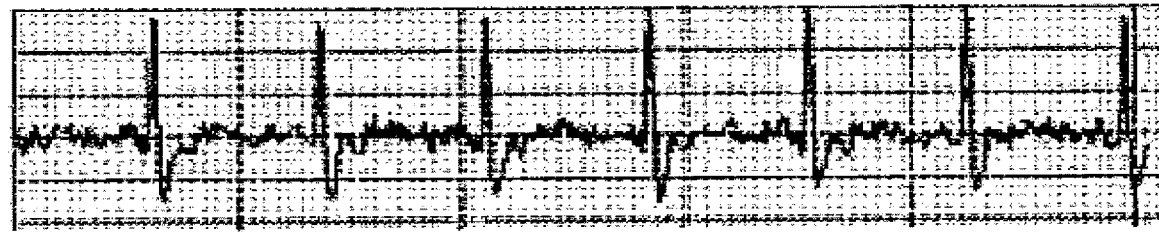
Figure 10C:
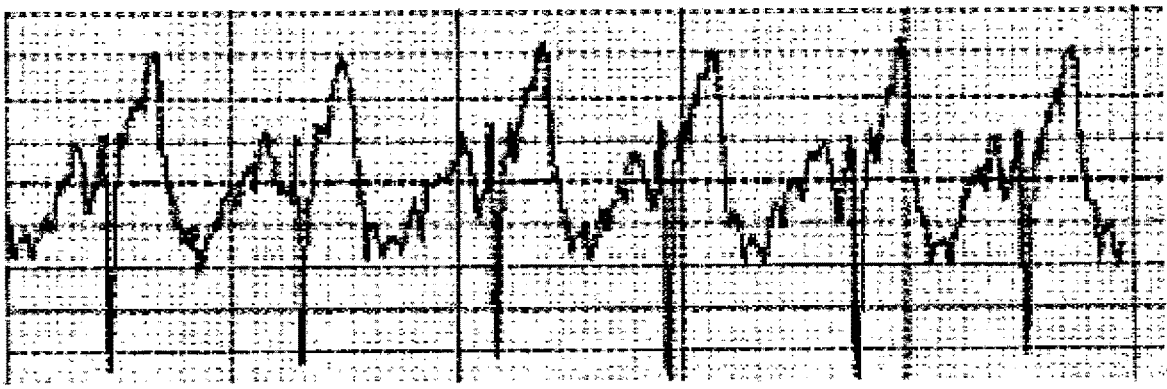

Please refer to FIG. 10a-FIG. 10d, electrode 1 on the chest cannot touch the body possibly, but electrodes (electrode 2 and electrode 3 are connected in parallel; electrode 2, electrode 3 and electrode 4 are connected to the positive and negative ends of ECG amplifier respectively) on the back are available obtain ECG, as shown in FIG. 10a. When the rider stops and stands on the road, electrode 1 on the chest touches the body providing that the rider does not bow; at this time, electrode 2 and electrode 3 are connected in parallel; electrode 1 and electrode 4 are connected in parallel; they are connected to the positive and negative ends of ECG amplifier respectively, so as to obtain ECG, as shown in FIG. 10b, for which, the R peak increases notably, but without P wave, as compared with FIG. 10a. From this, it can determine whether the rider is standing or bowing. Similarly, when the rider is seated on the bike with vertical upper part of the body, electrode 1 on the chest and electrode 5 one the buttock can be used to obtain ECG, as shown in FIG. 10c; when the rider stands, electrode 5 is not pressed by the buttock, thus ECG for the buttock disappear, which means the rider does not ride on the bike. See Table 3 for the judgment criteria of posture.

Figure 10D:
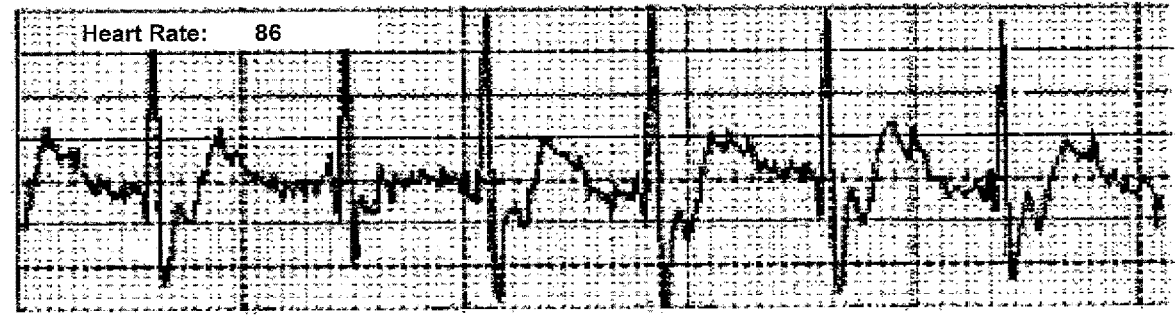

Electrodes may also be configured on trousers and stockings; electrode 6 and electrode 7 are configured near the knees, and respectively connected with a clip switch or tension sensor in parallel; electrode 8 and electrode 9 are configured on stockings, and respectively connected with a key switch in series; electrode 9 and electrode 7 are connected in series; electrode 6 and electrode 8 are connected in series; when the knees straighten and the feet contact the ground, electrode 8 and electrode 9 will be pressed, while electrode 6 and electrode 7 are not pressed, thereby, ECG (as shown in FIG. 10d) may be obtained by electrode 8 and electrode 9; when walking, the right or left knee bends to make electrode 6 and electrode 7 get through, thus different ECG may be obtained by the electrode on the other stocking. From this, we can see whether the rider is walking, standing statically or bending knees.

TABLE 3

| Position of electrode | Posture | P | +R | T | Figures |
|---|---|---|---|---|---|
| Jacket or trousers | Upper part of the body bends front | 1 | 1 | 1 | FIG. 10a |
| | Standing with erect upper part of the body | 0 | 1 | 0 | FIG. 10b |
| | Being seated on the bicycle | 1 | 0 | 1 | FIG. 10c |
| | Standing with erect upper part of the body | | | | |

TABLE 3-continued

| Position of electrode | Posture | P | +R | T | Figures |
|---|---|---|---|---|---|
| Trousers and stockings | Standing | 0 | 1 | 1 | FIG. 10d |

After capturing the ECG, the signal processor will judge the posture and then send the information to the personal information device which may give suggestions or alarms based on the preset range by the user. For instance, when the heart rate is too fast according to the ECG, the reason may be overload. If so, the rider will be suggested to slow down; when the posture and acceleration remain unchanged for long time, the reason may be that the rider falls off the bicycle and becomes unconscious. If so, the personal information device may send alarm to a person or organization far away via various wireless communication links (e.g. mobile phone or wireless network) to request assistance.

Preferred Embodiment 3

Figure 11A:
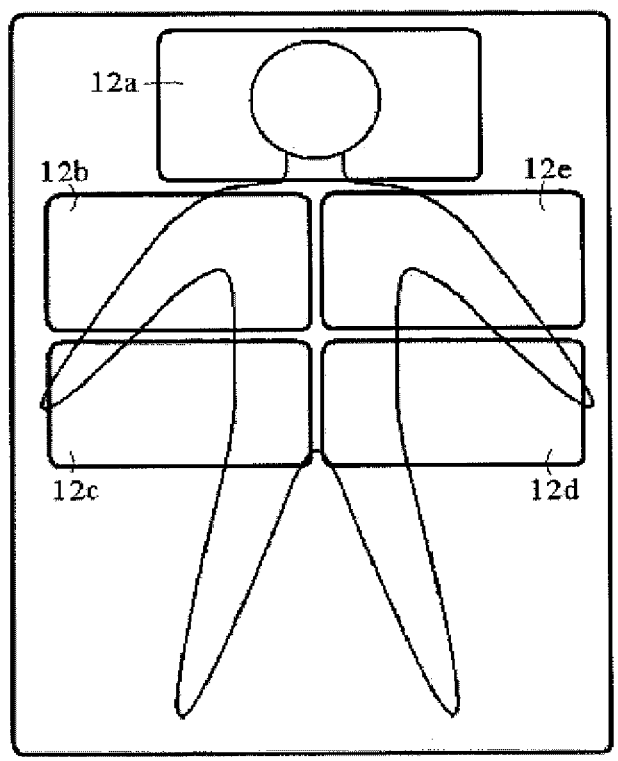
FIG. 11 illustrates the electrode position and connection diagram of the third preferred embodiment of the present invention when applied to a bed.
Figure 11B:
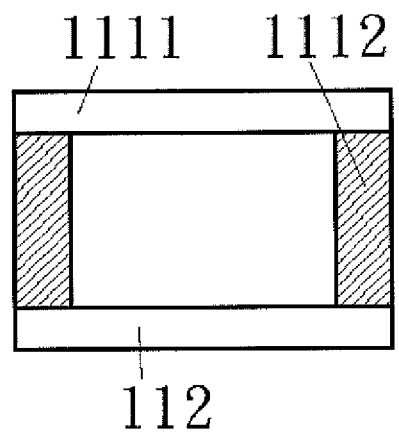

FIG. 11a illustrates the electrode position and connection diagram of the third preferred embodiment of the present invention when applied to a bed. The side view of the electrode is shown in FIG. 11b, wherein the key switch is also an electrode. When a key switch is pressed by human body, the resilient middle layer 1112 of the key switch is compressed so that the upper conductor 1111 contacts the lower conductor 112 and hence the ECG signal is capacitive coupled to 1111 than transmitted to 112 and connected to the input terminal of the amplifier. In preferred embodiment 3 of the present invention, electrodes 12a-12e touching the body are configured on specific positions on the bed, while a key switch or pressure sensor is provided; the section of circuits may refer to FIG. 1; the key switch or pressure sensor is provided on the clothes, as an electrode.

Electrode 12a and electrode 12b are connected to electrode 12d; electrode 12c and electrode 12e are connected, as the positive and negative input ends of the amplifier circuit; the input end of the amplifier circuit adopts capacitive coupling to obtain ECG signal via the key switch or pressure sensor; when the user has changed his/her sitting or sleeping position, the body will touch different parts of electrodes to cause various ECG waveforms. In this way, it is feasible to judge the position according to ECG waveforms. At this time, the processor is equipped on the bed.

Figure 12A:
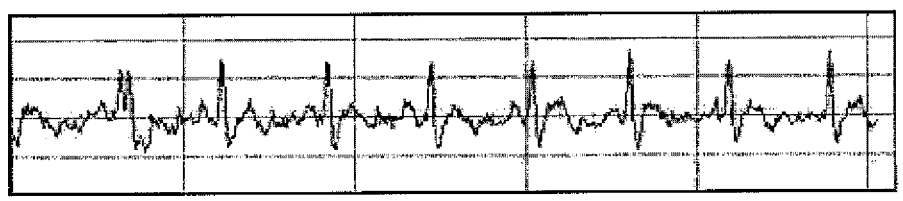
FIG. 12a-FIG. 12c illustrate ECG of various positions of the third preferred embodiment of the present invention.
Figure 12B:
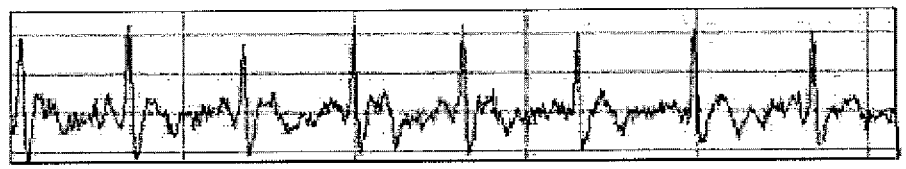
Figure 12C:
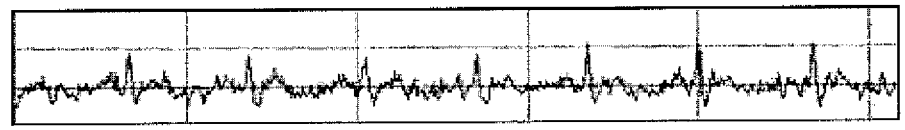

For example, when electrodes are configured on the pillow and bedspread, in case of different sleeping positions, the sleeper will press on different parts of electrodes on the pillow and bedspread, which causes various ECGs, as shown in FIG. 12a-FIG. 12c (FIG. 12a: Lie on the back, neck not touch the bed and legs lift; FIG. 12b: Lie on the back, neck touches the bed and legs lift; FIG. 12c: Lie on the back, neck touches the bed and legs keep flat). See Table 4 for the judgment criteria of posture.

TABLE 4

Figure 14A:
FIG. 14a-FIG. 14e illustrate ECG waveforms of various sitting positions of the fourth preferred embodiment of the present invention.
Figure 14B:

| | VS > k4 * VR | VT > k5 * VR | Figures |
|---|---|---|---|
| Lie on the back, neck not touch the bed and legs lift | 1 | 0 | FIG. 14a |
| Lie on the back, neck touches the bed and legs lift | 0 | 0 | FIG. 14b |

TABLE 4-continued

Figure 14C:
Figure 14D:
Figure 14E:

|  | VS > k4 * VR | VT > k5 * VR | Figures |
|---|---|---|---|
| Lie on the back, neck touches the bed and legs keep flat | 0 | 1 | FIG. 14c |

Wherein the k4 is from 0.5 to 0.7, preferably 0.6; k5 is from 0.2 to 0.4, preferably 0.3. It is possible that the key switch or pressure sensor is configured directly on the bedspread, with one end connected to the electrode on the bedspread, and the other end connected to the processor, which can achieve equal effect.

Preferred Embodiment 4

Figure 13:
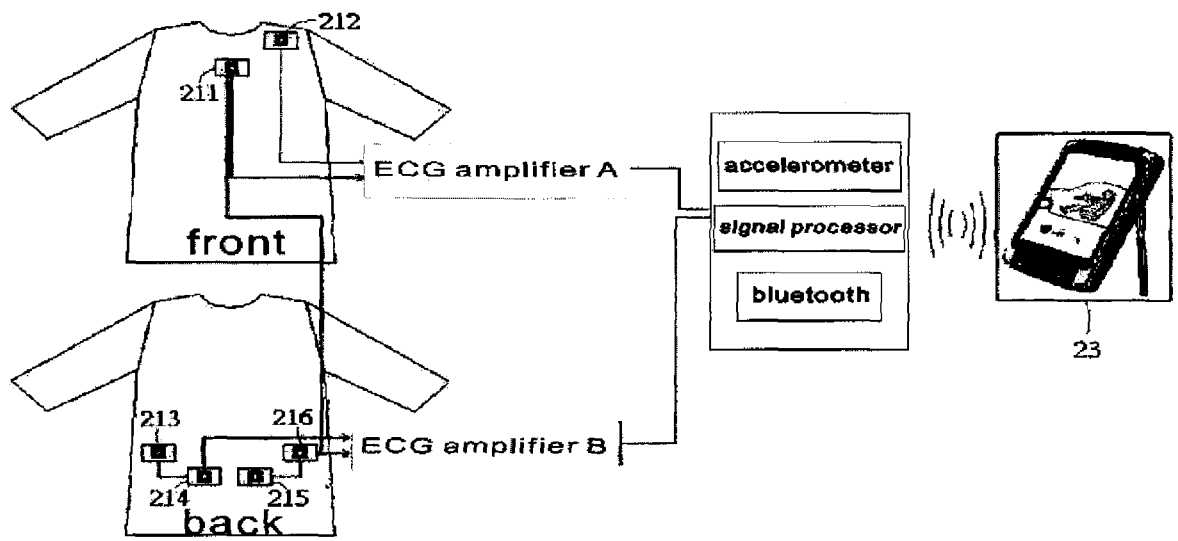
FIG. 13 illustrates the electrode position, connection and block diagram of the fourth preferred embodiment of the present invention when applied to the driver's seat.

FIG. 13 illustrates the electrode position, connection and block diagram of the fourth preferred embodiment of the present invention when applied to the driver's seat.

Every electrode is connected with a pressure sensor. In preferred embodiment 4 of the present invention, there are two electrodes (electrode 211 and electrode 212) on the chest; when the driver is sitting upright or bending front, electrode 212 will get through thanks to the pressure by the seat belt, except for bending left. Electrode 211 will get through as long as the driver is buckled up. See Table 5 for electrodes enabled in case of various sitting positions (sitting upright, bending front, bending right, bending left and not buckled up)) and seeing whether or not the two ECG amplifiers obtain ECG signals (determined by whether or not there is R peak), the obtained ECG waveform is as shown in FIG. 14. Electrodes 1-6 in Table 5 are corresponding to electrodes 211-216 in Table 5 respectively.

TABLE 5

|  |  | Electrode | | | | | | | |
|---|---|---|---|---|---|---|---|---|---|
|  |  | ECG amplifier A | | | ECG amplifier B | | | | |
| Buckled up or not | Posture | 1 | 2 | ECG | 3 | 4 | 5 | 6 | ECG |
| Yes | Bending front | + | + | Yes | − | − | − | − | No |
|  | Sitting upright | + | + | Yes | − | + | + | − | Yes |
|  | Bending right | + | + | Yes | − | − | − | + | No |
|  | Bending left | + | − | No | + | − | − | − | Yes |
| No | Sitting upright | − | − | No | − | + | + | − | Yes |
|  | Others | − | − | No | − | − | − | − | No |

From Table 5 and FIG. 13, it is easy to judge the driver's sitting position. With few exceptions, it must judge the driver's sitting position according to waveforms under conditions of "bending left and buckled up" and "sitting upright and not buckled up"; for other cases, it is able to judge the driver's sitting position by confirming whether or not ECG is outputted by ECG amplifier A or B and whether there is R peak (with reference to the table). It is pretty easy to recognize "bending left and buckled up" and "sitting upright and not buckled up"; for the former, there is a huge T wave approximate to R peak; for the latter, there is a small T wave according to VT>k6*VR; similarly, it is very easy to recognize "bending front and buckled up" and "bending right and buckled up"; for the former, there is a huge T wave; for the latter, there is a small T wave according to VT>k6*VR; wherein the k6 is from 0.7 to 0.9, preferably, 0.8.

Because emergency brake or a hole is inevitable during driving, if so, the ECG will seriously distorted or even hard to read due to violent movement of the body. The present invention may get rid of these abnormalities by using an accelerometer. After actual test for many times, the conclusion is obtained: When the instantaneous acceleration is more than 9.8 m/second 2 (gravity acceleration of the earth surface, g), the ECG will seriously distorted or even hard to read. For this reason, the method disclosed by the present invention comprises capturing the signal of the accelerometer, and stopping analyzing ECG to prevent wrong judgment when the acceleration is more than 9.8 m/second 2.

Preferred Embodiment 5

Figure 15:
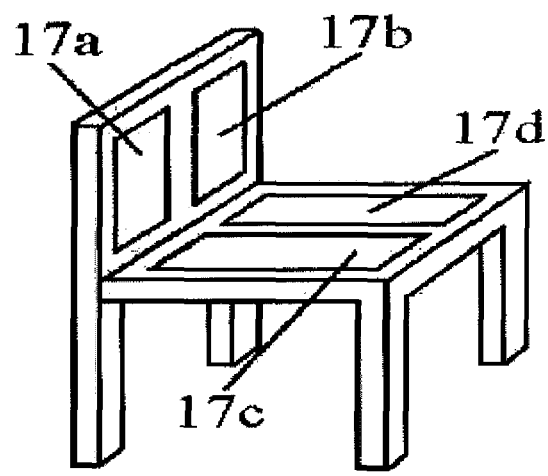
FIG. 15 illustrates the electrode position of the fifth preferred embodiment of the present invention when applied to a chair.
Figure 16A:
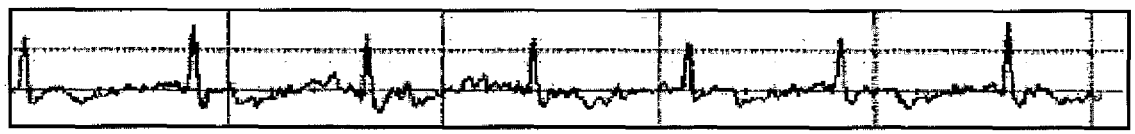
FIG. 16a-FIG. 16d illustrate ECG of various positions of the fifth preferred embodiment of the present invention.
Figure 16B:
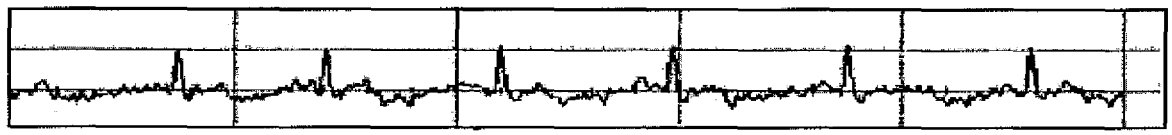
Figure 16C:
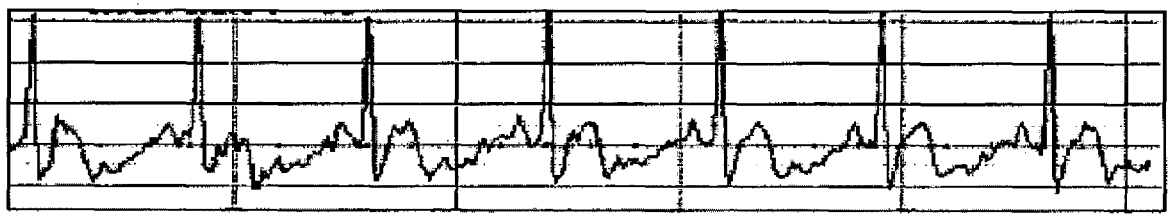
Figure 16D:
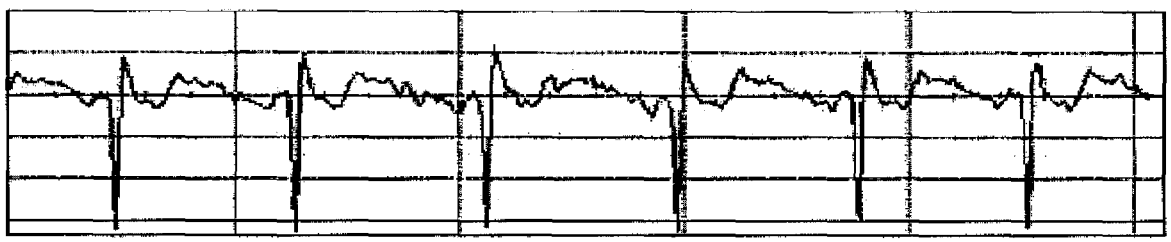

FIG. 15 illustrates the block diagram of the fifth preferred embodiment of the present invention when applied to a chair. Electrode 17a is connected to electrode 17d and a key switch or pressure sensor in turn; electrode 17b is connected to electrode 17c and a key switch or pressure sensor in turn, as well as to the positive and negative input ends of the signal processor respectively to obtain ECGs, as shown FIG. 16a-FIG. 16d. ECGs for various sitting positions are as follows: FIG. 16a: Sitting upright and leaning against the chair; FIG. 16b: Sitting upright, not leaning against the chair; FIG. 16c: Sitting left; FIG. 16d: Sitting right; by comparing FIG. 16a with FIG. 16b, it can be known that amplitudes of R and S are bigger in FIG. 16a. When sitting right and left, the ECGs (as shown in FIG. 16c and FIG. 16d) include apparent T wave, while no T wave when sitting upright. When sitting right and left, we can see R peak has contrary direction, which helps to judge the position. See Table 6 for the judgment criteria of posture.

Moreover, an electrode may be configured on the jacket, while a key switch or pressure sensor is on the chair to connect a processor; when the electrode on the jacket gets through and touches the key switch or pressure sensor, the ECG signal will be sent to the processor.

TABLE 6

|  | VS > 0.3 * VR | R+ | VT > 0.2 * VR |
|---|---|---|---|
| Sitting upright and leaning against the chair | 1 | 1 | 0 |
| Sitting upright, not leaning against the chair | 0 | 1 | 0 |
| Sitting left | 0 | 1 | 1 |
| Sitting right | 1 | 0 | 0 |

Figure 17:
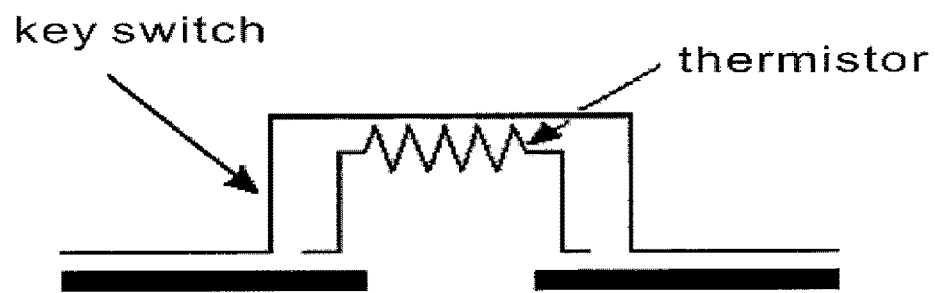
FIG. 17 illustrates the diagram of the temperature sensor of the sixth preferred embodiment of the present invention.
Figure 18:
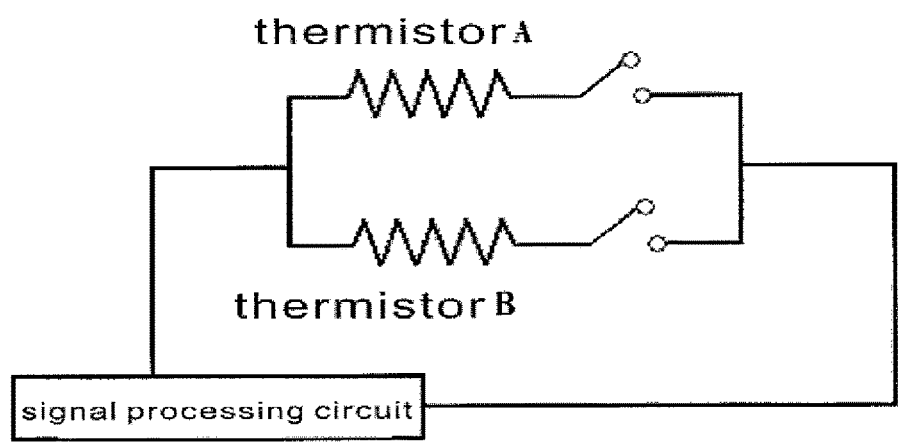
FIG. 18 illustrates equivalent circuits of the temperature sensor of the sixth preferred embodiment of the present invention.

Preferred Embodiment 6 the non-posture sensor is a temperature sensor (e.g. thermistor) and connected with a key switch, tension sensor or pressure sensor, it is able to measure temperature and judge position. For example, four types of thermistors are adopted, of which the nominal resistances at ambient temperature are 10K, 20K, 40K, and 80K Ohms, and the ratio of variation within body temperature range (32° C.-40° C.) is about 5% such that the resistance of each thermistor will not be the same. Each thermistor is serial connected with a key switch, then parallel connected to the input terminal of the processor. The four thermistors are positioned on back, chest, right side, and left side of the body. Because that the resistance of each thermistor will not be the same, the processor can determine which key switch is pressed such that the posture can be judged. Once the object touching body presses the temperature sensor will begin to touch the body directly to cause the temperature there to rise to an approximate body temperature. Meanwhile, in the present invention, thermistors with different resistance values may be positioned in series or parallel on different parts; in this way, the signal processor can determine whether there is pressure in order to judge position, block diagram as shown in FIG. 17, wherein the key switch is also a temperature sensor, and equivalent circuit as shown in FIG. 18. For example, when a thermistor (with resistance of about 6K Ohms under body temperature and 10K Ohms under ambient temperature, and β about 3500) is positioned on back, and another thermistor (with resistance of about 12K Ohms under body temperature and 20K Ohms under ambient temperature) is positioned on chest, it is able to judge four positions if only the resolution of analog-digital conversion of the processor is relatively high (e.g. 12 bits) by determining whether there is pressure on each thermistor. Serial or parallel connection of sensors has benefits of reducing the number of nodes to the processor so as to reduce the number of nodes between the object and processor, finally to make the user feel more comfortable as if there is no sensor.

In addition, the temperature sensor may be positioned in materials of different thickness or thermal coefficient, thus the accuracy and diversity of judging posture is increased thanks to the difference of heat conduction speed.

Preferred Embodiment 7

Figure 19:
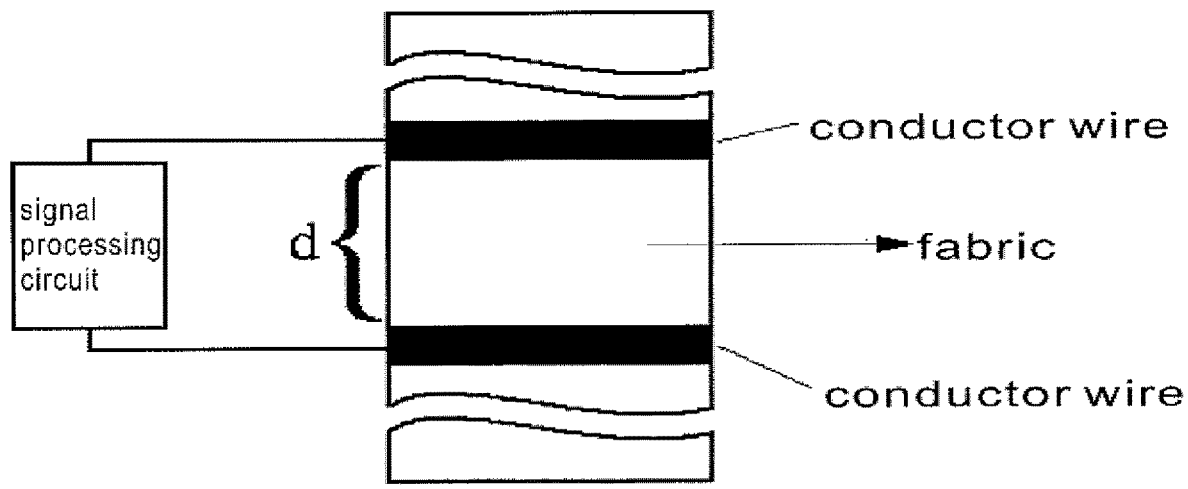
FIG. 19 illustrates the diagram of the sweat sensor of the seventh preferred embodiment of the present invention.

In another embodiment, a sweat sensor is coupled with a switch, tension sensor or pressure sensor to detect the body sweat, for which, the mechanism is measuring DC resistance between two metal leads; as the sweat may cause conductivity, lower resistance, more sweats, as shown in FIG. 19. There are more sweats when a switch, tension sensor or pressure sensor which gets through is placed where the external object touches the body. It is able to obtain different resistances on different parts to judge position by placing the sweat sensor on hygroscopic materials of different thickness. For instance, as shown in FIG. 19, d is the distance between two metal leads; six leads (the d is 1, 2, and 3 cm respectively) are sewed on the fabric, which will get through due to external force, sharing a switch, pressure sensor or tension sensor. When the sweat sensor at 1 cm distance cannot read for it is sweating thoroughly, the sweat sensor at 2 or 3 cm distance will work; a variety of sweat absorption materials of different thickness may be adopted to provide diversity of sweat sensors; providing that the sweat sensor is placed together with the electrode, sharing a switch, pressure sensor or tension sensor, it is possible to obtain ECG signal and learn how it is sweating at the same time; when there are few sweats, the skin is too dry and ECG is hard to read because of too much noise; when it is sweating heavily, the ECG will be fairly distinct; according to this, ECG signals with low S/N ratio will be excluded to increase the accuracy of judging the position; besides, addition of a pressure sensor or tension sensor enables to reduce noise interference; the S/N ratio for the ECG is various due to different pressure, that is, more pressure, more distinct the ECG is; where a sweat sensor, temperature sensor and a pressure sensor or tension sensor is available at the same time, it can not only analyze the position, but also obtain ECG signals, yet it is hard to obtain ECG signals when the skin is too dry at low temperature.

Preferred Embodiment 8

What's more, an electrode may be coupled with a switch, tension sensor or pressure sensor to obtain EMG to detect the muscle (pressed parts in particular) contraction. For instance, when squatting, the EMGs for the pressed parts of legs and buttocks are very distinct. In a similar way, the pulse may be measured by plethysmography, or level of subcutaneous fat by a capacitive body fat analyzer, or blood oxygen concentration, pulse or blood pressure by a photodetector. It may be different material or thickness between the non-posture sensor and the body to generate various characteristics of signals.

Preferred Embodiment 9

In the present invention, two different non-posture sensors may be coupled with a switch, tension sensor or pressure sensor to detect physiological signals and positions of a person. For example, when sleeping, electrodes may be put on chest and back, while a temperature sensor under right and left armpits, so it is able to obtain ECG distinctly when the user lies on chest or back; however, it is unable to obtain ECG signal when the user lies right or left, unless the user's hands touch the electrodes on the clothes, but it is able to measure the temperature of right and left armpits rise to approximate body temperature. Materials of different thickness or thermal coefficient are used to separate the sensor from the body. In this way, not only body temperature and ECG signal, but also the position can be judged without complicated signal processing.

Furthermore, more than one different or same non-posture sensors may share a pressure sensor or tension sensor as a result in reducing the number of the pressure sensor or tension sensor. For example, the same key switch or clip switch can be provided for two different or same non-posture sensors. The non-posture sensors are ECG, EMG, respiration, impedance pneumography, sweat, EEG, body fat, swallow, cough, speaking, blood pressure, pulse, capacitive respiration, blood oxygen and blood sugar sensors which share the switch, pressure sensor or tension sensor. A same critical value can be set to start the connected physiological sensors or close the object currently detected.

Preferred Embodiment 10

In the present invention, the accuracy of judging positions may be increased by the synergy of diversified sensors or the variation rate of signals. For example, in the previous embodiment, once the acceleration is too much according to the accelerometer, it means the ECG or other signals are seriously distorted due to interference. In the present invention, the critical value of the accelerometer may be set in consideration of different applications (e.g. the critical value is 9.8 m/second2 in preferred embodiment 4); if it exceeds the critical value, analysis will be stopped for the time being to prevent wrong judgment. Besides, the body temperature or posture will not change abruptly in a very short time; in this sense, where the signal processor acquires a dramatic signal irrationally, it may be caused by external interference or incorrect operation. In a similar way, in the present invention, the critical value of the variation rate may be set in consideration of different applications, which may be deemed as a criterion for screening abnormal signals. If abnormal signals are received frequently, an alarm may be sent to the user. Finally, it is possible to weight the connected physiological sensor with the value of the pressure sensor or tension sensor, or the value of a different pressure or strain, because the ECG waveform is amplified at a different scale under condition of different pressure sensor or tension sensor.

Preferred Embodiment 11

The present invention can send an alarm at the right moment to maintain health and safety of the user. For example, for a bicycle rider, high body temperature and fast heart rate for long time may represent sunstroke or overload. When analysis and storage of signals, as well as comparison with the database are not available through the signal processor, the displays and alarms may reach PDA or personal computer 12 via wireless transmission for the purpose of processing, comprising, firstly setting a normal range of physiology of the user in the activity; sending alarms to the user or to a person or organization faraway via a communication device like PDA or personal computer 12 once it is beyond this range; or sending the physiological signal to the remote end and judging whether the physiological function is beyond the normal range by referring to the remote user physiological signal database, so as to determine whether an alarm should be sent; moreover, PDA or personal computer 12 may provide appropriate instructions to the user directly.

Preferred Embodiment 12

Figure 20A:
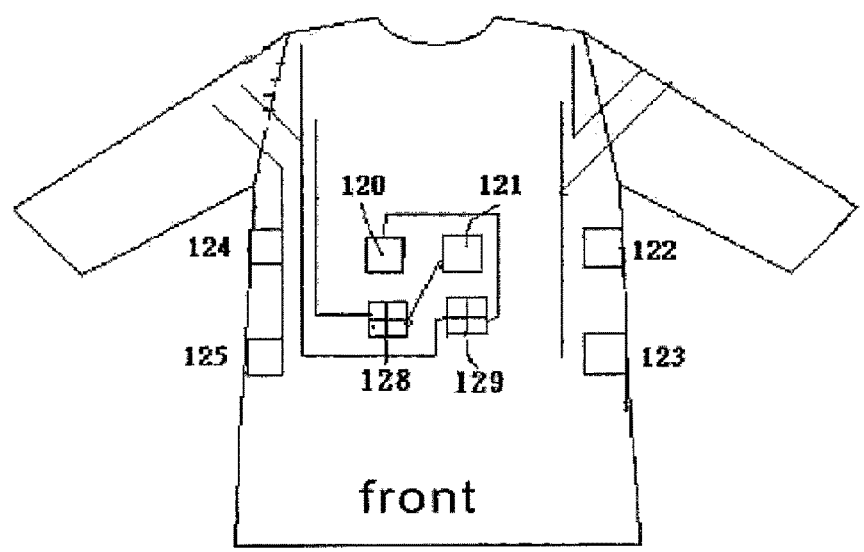
FIG. 20a-FIG. 20b illustrate connection diagram of a pressure sensor or tension sensor to different parts of clothes of the twelfth preferred embodiment of the present invention.
Figure 20B:
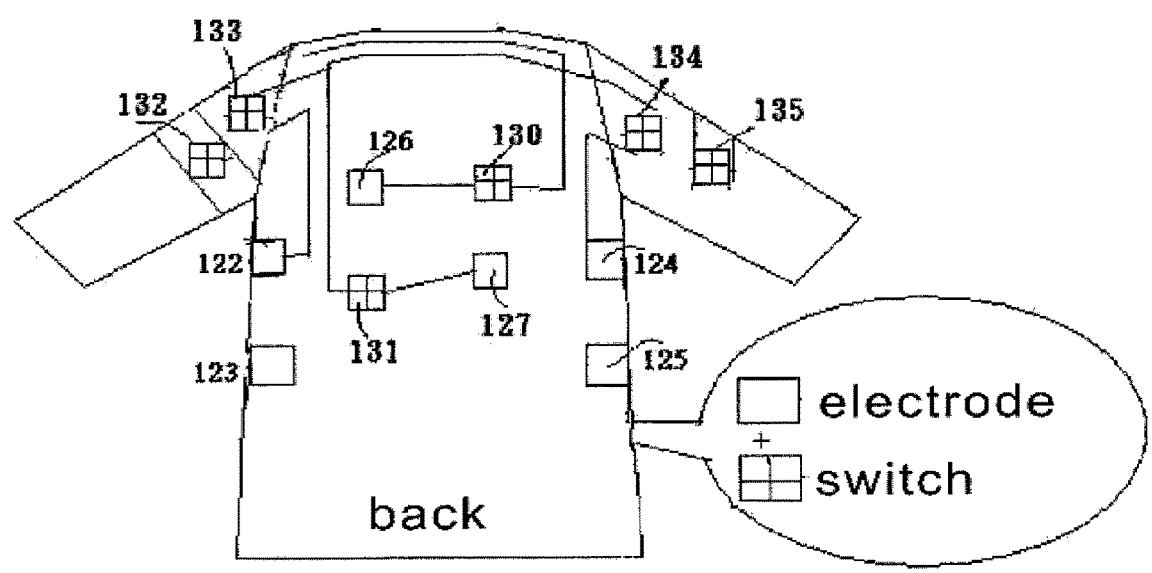

Starting, closing or changing the working mode of the present invention can be realized by either the user or other ways. For example, when one end of the pressure sensor or strain gauge on the clothes, chair or bed is made to connect to the signal processor via a lead, and the other end to the non-posture sensor, it is possible to start or close another object in contact after the user puts on clothes, sits on the chair or lies on the bed. Alternatively, it starts immediately when some signal such as RFID or tag is received via the wireless device of the signal processor. The automatic operation can realize benefits of ensuring the user's daily schedule and operation of the present invention under normal working mode, saving electricity and prolonging working hours as well. Please refer to FIG. 20*a*-FIG. 20*b* for embodiment 20 of the present invention, electrodes are not connected to the pressure sensor or strain gauge below directly, but connected to the pressure sensor or strain gauge on different parts of the clothes. For example, the original electrodes on the clothes keep "as is", yet the pressure sensor is moved away. For instance, the right pressure sensor below the electrode is moved to the shoulder and connected to the physiological sensor in the waist. When the user lies on right or left, the pressure sensor on the shoulder and electrode in the waist will surely be pressed, that is, when the user lies on left, the processor will read the signal on the left, as the pressure switch on the left is pressed; whereas, there are no signals for other three parts even though electrodes on other three parts are connected a pressure sensor which is not pressed, the signal cannot be sent to the processor. By the same way, a pressure sensor, key switch, or tension sensor positioned at right shoulder is connected between the electrode positioned at other site and the ground wire. When the user lying on right side and other pressure sensor, key switch, or tension sensor is pressed by mistake, the quality of the signal is still not affected, because the unexpected electrode is connected to ground wire. The physiological sensor is also connected to switches in different areas (the switches are used as a pressure sensor or strain gauge), in a bid to prevent contact with the physiological sensor by mistake and influence on the quality of the signal after contact with the physiological sensor by mistake. The switches and pressure sensor or strain gauge are not enabled, as a result it can save electricity, detect for long time and decrease the chance of signal processing in case of contact by mistake. An air or a water filling device is near the physiological sensor, which is connected to the processor electrically. After the processor sends signals, the physiological sensor will touch the body more closely. The air or water filling device may also be coupled with the switches and pressure sensor or strain gauge directly. If so, the switches and pressure sensor or strain gauge are hermetic. When the physiological signal quality is inferior under external force, the air or a water filling device will force the physiological sensor to touch the body more closely so as to reduce noise. In case of over pressure or strain, the air or water filling device will discharge air or water to reduce pressure or strain to make the user comfortable.

Preferred Embodiment 13

Conventionally, two or three electrodes will be adopted to detect ECG. In case of three electrodes, the third electrode is grounding. We can recognize whether ECG is obtained by two or three electrodes according to ECG signals, and in other words can learn the change in the user's position. For example, after the third electrode connected to a switch is configured on the right hip joint, when the user is sitting down, the ECG features three electrode signals; when the user is standing, the ECG features two electrode signals for the third electrode is not pressed; use of some switch connected to the third electrode will enables to detect the position more accurately, that is, a switch or pressure sensor is connected to the third electrode; when the user is sitting down, the switch is pressed, while the third electrode is forced to connect to the processor, so the ECG features three electrode signals; if the switch is not pressed, the third electrode will not be forced to connect to the processor, thereby the ECG features two electrode signals. Consequently, on one hand, we can determine whether ECG is obtained by two or three electrodes, and on the other hand, can detect the change in the user's position.

Preferred Embodiment 14

The above mentioned are examples of connection of the non-posture physiological sensor with a switch and pressure sensor or tension sensor. Actually, the non-posture physiological sensor may be connected with certain treatment device, namely, heating, cooling, TENS devices, or an electrode. In this way, the processor may initiate the treatment device for treatment or health care in case any abnormal physiological signal occurs. The switch and pressure sensor or tension sensor can be fixed with the felt on the cloth. The conductive areas on the cloths and accessories will get through under external force and restore immediately when the external force disappears. Electronic components (such as resistor, LED or other sensors like temperature sensor or ECG electrode) or treatment device (such as heating, cooling, TENS devices) may be provided for the accessories.

Preferred Embodiment 15

In the foregoing examples, the non-posture physiological sensor and the switch, pressure sensor, pressure applicator or strain gauge may be deployed on two different fabrics, while the non-posture physiological sensor will begin to contact the switch, pressure sensor, pressure applicator or strain gauge due to external force. That is to say, the non-posture physiological sensor is configured on one fabric and the switch and pressure sensor or strain gauge on another fabric; meanwhile, the processor is electrically connected to the non-posture physiological sensor or the switch.

Figure 23A:
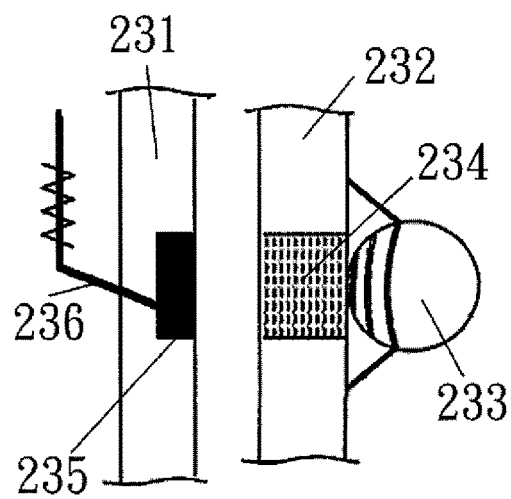
FIG. 23a-FIG. 23b illustrate the diagram of physiological sensor and a pressure sensor positioned on different fabrics of the fifteen preferred embodiment of the present invention

As shown in FIG. 23a, a thermistor 236 is positioned on underclothes 231 and a pressure sensor positioned on shirt 232 comprised by a two-section switch 233 and conductor 234. When the user sits or lie down such that the switch 233 connects both conductor 234 on the shirt and 235 on the underclothes, and hence the thermistor is connected to the processor and body temperature can be obtained.

Figure 23B:
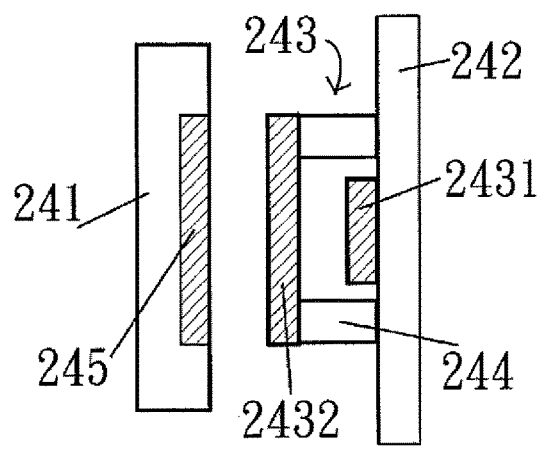

Another example is shown in FIG. 23b, wherein a capacitive coupling electrode 245 is positioned on underclothes 241, and a switch 243 positioned on a shirt 242. Switch 243 is comprised of upper conductor 2432, a resilient layer 244 and lower conductor 2431. When the user sits or lie down such that the resilient layer 244 is compressed such that lower conductor 2431 is connected with upper conductor 2432 and 242 contacts 241 such that upper conductor 2432 contacts electrode 245 hence the processor can obtain ECG signal.

Figure 24A:
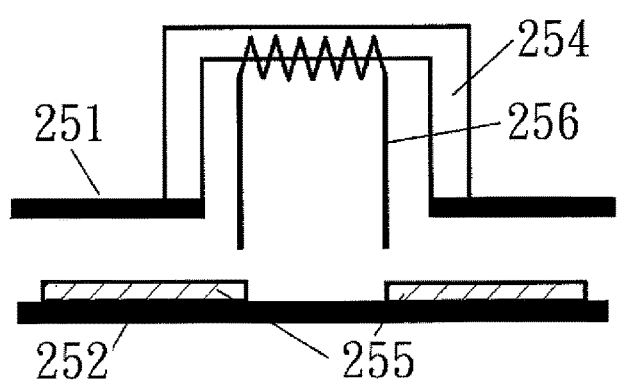
FIG. 24a-FIG. 24b illustrate the diagram of a pressure sensor divided into two part and positioned on different fabrics of the fifteen preferred embodiment of the present invention
Figure 24B:
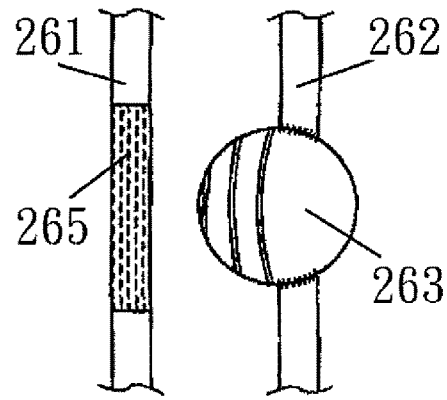

Alternatively, the switch, pressure sensor or tension sensor is divided into two parts, where each part is positioned on different fabrics but will contact due to external force and one of the two parts is electrically connected to a physiological sensor or processor. As shown in FIG. 24a, a thermistor 256 is installed in the resilient layer of a switch positioned on underclothes 251, and the both terminals of thermistor 256 is used as the upper conductor of the switch, while the lower conductor 255 is positioned on shirt 252. When the user sits or lies down, the resilient layer 254 is compressed such that the lower conductor 255 is connected with thermistor 256, and hence the processor can obtain body temperature. Another example is shown in FIG. 24b, wherein an electrode 265 is positioned on underclothes 261 and also a part of the pressure sensor. The other part of the pressure sensor is a two section switch positioned on a shirt 262. When the user sits or lies down such that the underclothes 261 and the shirt contact each other such that the electrode 265 which contacts the user can generate ECG signal and transmit it to the processor.

Preferred Embodiment 16

Figure 21:
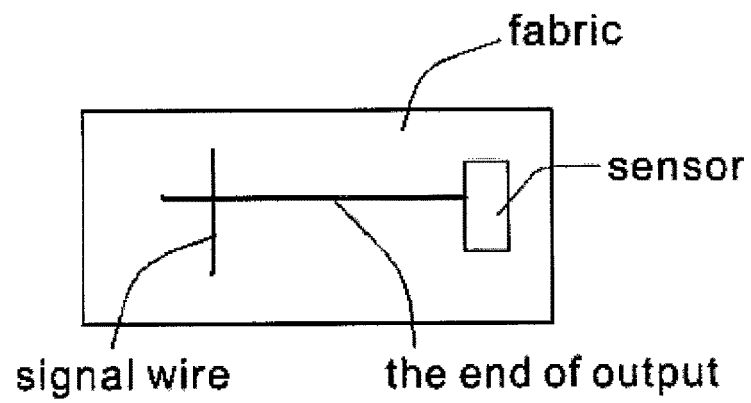
FIG. 21 illustrates connection of sensors with signal wires.
Figure 22:
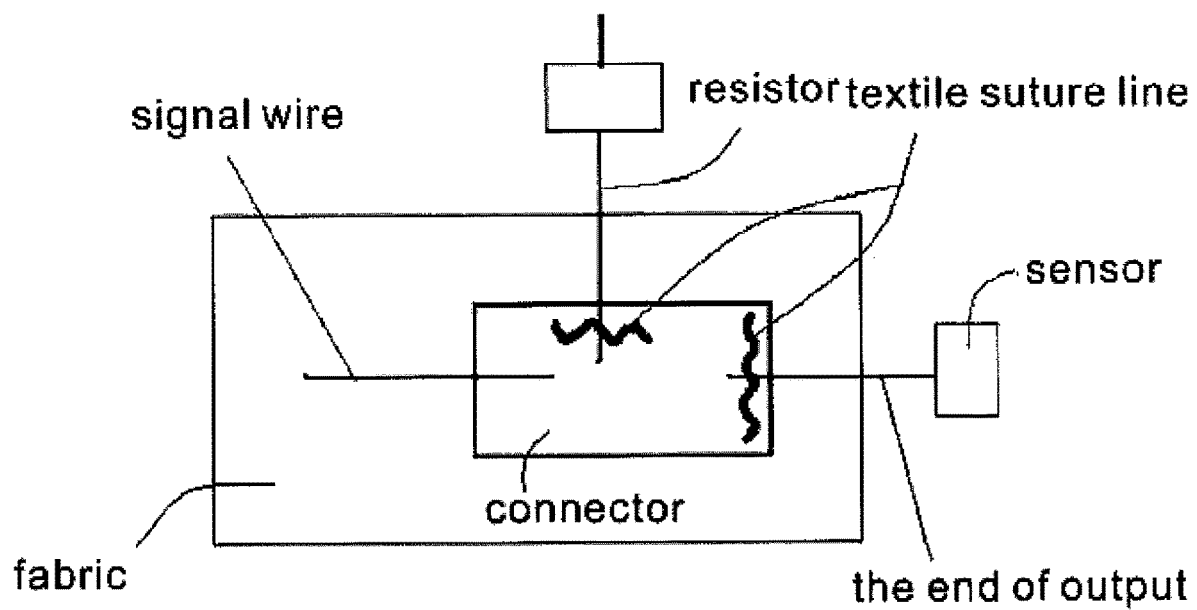
FIG. 22 illustrates stitching of sensors with signal wires

In most of the time, the sensor is connected with the signal wire by sewing instead of welding to protect environment. However, it is somewhat difficult to directly connect the output end of the sensor to the signal wire by sewing. As shown in FIG. 21, the nodes are prone to become apart after cleaning. For this reason, there is certain conductive material on the fabric below the output end of the sensor, which serves as a connector. The output end of the sensor is fixed with the connector by sewing (plain weaving, knitting, tatting, and so forth). The connector is intrinsically a part of the fabric or becomes a part by weaving, as shown in FIG. 22. As a kind of conductive material, the connector gets through the output end of the sensor by the threads which may be made of either conductive material or nonconductive material; moreover, the signal wire is connected to other sensors or electronic component such as processor via the connector by plain weaving, knitting, tatting, and so forth Certainly, another electronic component such as resistor may be sewed on the connector. The edges of the connector are as follows: 1. It is easy to produce a connector; 2. It is easy to detect faults of the electronic component or sensor; 3. The electronic component or sensor can be replaced simply in case of faults; 4. The connector may be shared by more than one components with one signal wire; 5. It is convenient for maintenance in case of faults of the connector and signal wire by sewing another connector or signal wire on the connector 2 or signal wire 4; 6. The entire system is formed by more than one connectors connected; 7. The sensors or electronic components on different fabrics may be connected to and share one connector.

Preferred Embodiment 17

Pressure applicator and physiological sensor may also used to generate ECG. For example, two container containing liquid are put on both shoulders respectively as pressure applicator, while the cloth under the pressure applicator are made of conductive materials as electrodes; when the user is standing, sitting or walking, the electrodes on both shoulders will become closer with the shoulders due to the pressure of the liquid, so as to obtain ECG.

If the area covered by the pressure applicator is larger enough, the liquid will occupy the lower part of the container such that the pressure applicator will press the electrode more close to the human body. When the user lies, the electrodes will not become close with the shoulders due to the gravity, thus it is unable to obtain ECG; in a similar way, when the user lies on back, the electrodes on chest will become closer with the chest due to the pressure of the liquid, so as to obtain ECG; when the user lies on sides or stands, it is unable to obtain ECG. Besides, if electrodes and pressure applicators are positioned on chest, the ECG waveforms are different when the user lies on back and stomach, because the heart moves down to be away from the electrodes when the user lies on back, and the heart is close to the electrodes when the user lies on stomach. Similarly, electrodes and pressure applicators can be positioned on shoulders, chest, upper and lower part of left side to obtain ECG signal, from the electrodes and pressure applicators on shoulders while standing or sitting; from those on chest while lying on stomach or back; from those on upper and lower part of left side while lying on sides. In addition, the posture of the user can also be judged by analyzing the ECG waveform.

In order to obtain ECG by three electrodes, a pressure applicator is put around the cloth on legs, and the cloth is made of conductive material; in doing so, no matter how the sleeping position of the user is changed, electrodes will contact partly with the legs to obtain ECG; the electrodes may be replaced by such sensors as temperature and respiration sensors.

For the above, the mechanism is that the weight of the liquid will exert different pressure on the physiological sensor with the change in the body position. For instance, a 50 g water pressure applicator has 50 g pressure on the shoulder, yet the pressure is "0" when lying down; in this sense, the pressure applicator will have a different pressure due to the change in the body position; by comparison, the aforesaid pressure sensor requires external force to produce pressure that enables the physiological sensor to detect physiological signals of the body; the pressure applicator may be connected to a motor to increase or decrease liquid, or substituted by a solid nonmetal or metal, for example, steel rod, ball or sand can be used, which can also increase the conductance of the electrode or it can be used alone as an capacitive coupling electrode.

For the above, the mechanism is that the weight of the liquid will exert different pressure on the physiological sensor with the change in the body position. For instance, a 50 g water bag has 50 g pressure on the shoulder, yet the pressure is "0" when lying down; in this sense, the bag will have a different pressure due to the change in the body position; by comparison, the aforesaid pressure sensor requires external force to produce pressure that enables the physiological sensor to detect physiological signals of the body; the bag may be connected to a motor to increase or decrease liquid, or substituted by a solid metal or nonmetal.

The above description is only about preferred examples of embodiments of the invention, and is not intended to limit the scope of the invention in any form. Even though this invention is described using several preferred examples mentioned above, these examples are not to be used to limit the scope of this invention. Those skilled in the art can make modifications or variations that are equivalents based on the above examples, without departing from the scope of the invention. Any embodiments that do not depart from the scope of the invention, and are based on the technical essence of this invention, having simple modification, equivalent variations or modifications, are still included in the scope of the invention.

What is claimed is:

1. A method for detecting a non-posture physiological function and a posture status of a user, the method comprising:
    providing at least two non-posture physiological sensors on an object configured to be in contact with the body of the user directly or indirectly;
    the at least two non-posture physiological sensors sensing the non-posture physiological function of the user; and
    a signal processor processing the non-posture physiological function to determine the posture status of the user by comparing amplitudes and polarity of the non-posture physiological function with posture characteristics and parameters of judgment criteria stored in a database of body positions;
    where the at least two non-posture physiological sensors comprise ECG electrodes and wherein the non-posture physiological function is an ECG function sensed by the ECG electrodes;
    wherein the step for processing the non-posture physiological function comprises; finding out a polarity of at least one point of P, Q, R, S and T of the ECG function, and amplitudes of the points P, Q, R, S and T, while reverse connecting at least one ECG electrode to produce inverse polarity; and
    wherein the judgment criteria is difference between amplitudes of at least two of P, Q, R, S and T on ECG.

2. The method for detecting a non-posture physiological function and a posture status of claim 1, further comprising:
    determining a deepness of sleep or consciousness status from the non-posture physiological function,
    wherein the deepness of sleep or consciousness status is deduced by the changing of a noise level of the non-posture physiological function acquired by the at least two non-posture physiological sensors;
    wherein an increase of noise represents an increase of consciousness or light sleep, while a decrease of noise represents a decrease of consciousness or deep sleep;
    wherein the noise is caused by separation between one of the at least two non-posture physiological sensors and skin; and
    wherein a contact between the body and one of the at least two non-posture physiological sensors is changing constantly in light sleep.

3. The method for detecting a non-posture physiological function and a posture status according to claim 1, wherein one of the at least two non-posture physiological sensors starts sensing when the signal processor receives RFID signal or tag signal.

4. The method for detecting a non-posture physiological function and a posture status of claim 1, wherein the database comprises posture characteristics and parameters of judgment criteria,
    Wherein the parameters of judgment criteria are data acquired by a motion sensor when the user is prompted by a guide to take different postures, and
    wherein the motion sensor is one selected from a group consisting: an accelerometer, a gyroscope, a tilt sensor, a fabric capacitance sensor and a video camera.

5. The method for detecting a non-posture physiological function and a posture status of claim 1, further comprising connecting the at least two non-posture physiological sensors in series or parallel.

6. The method for detecting a non-posture physiological function and a posture status of claim 1, further comprising: forming an actigraph using the determined posture status.

7. The method for detecting a non-posture physiological function and a posture status of claim 1, wherein the object for arranging the at least two non-posture physiological sensor comprises: clothes, underclothes, coat, bedspread, pillow, stockings, shoes, scarf, kerchief, gloves, apron, belt, carpet, floor map or chair.

8. The method for detecting a non-posture physiological function and a posture state according to claim 1, wherein the step for sensing the non-posture physiological function further comprises: capturing a signal from at least one posture sensor at the same time as the at least two non-posture physiological sensors; when signal from the at least one posture sensor is stronger than a specific critical value, stopping the processing non-posture physiological signal to prevent wrong judgment; wherein the at least one posture sensor is accelerometer, gyroscope, fabric capacitance sensor or video camera.

9. The method for detecting a physiological function and a posture state according to claim 1, further comprising: using a wireless communication device for transmitting the posture status or the non-posture physiological function processed by the signal processor to a personal information device, or the personal information device sending the posture status or the non-posture physiological function to an organization at remote end.

10. The method for detecting a non-posture physiological function and posture state according to claim 1, wherein a capacitor, resistor or an inductor is selectively connected in series or parallel between the at least two non-posture physiological sensors and the signal processor to consider the characteristics of body impedance and signal frequency.

11. The method for detecting a non-posture physiological function and a posture status of claim 1, wherein signals sensed by the non-posture physiological sensor are negative polarity for one posture and are positive polarity for the other posture.

12. The method for detecting a non-posture physiological function and a posture state according to claim 1, wherein the ECG sensors are either only two electrodes or only three electrodes.

13. An object for detecting a non-posture physiological function and a posture status of a user, the object comprising:
    at least two non-posture physiological sensors adapted to contact with the user's body directly or indirectly;

wherein the at least two non-posture physiological sensors are adapted to sense a non-posture physiological function of the user to generate non-posture physiological signals; and a signal processor configured to determine different body position or posture of the user by generating posture characteristics from the non-posture physiological signals and referring to a judgment criteria;

wherein at least one of the at least two non-posture physiological sensors is a temperature sensor;

wherein the at least two non-posture physiological sensors are placed in the object comprising materials of varying thickness or varying thermal conductivity, such that the temperature sensor placed in the object is adapted to detect non-posture physiological signals for determining body position or posture of the user based on different resistances or heat conduction speed of said materials having said varying thickness or different varying thermal conductivity.

14. The object for detecting a non-posture physiological function and a posture status of claim 13, wherein the object is loosely wearable on user body and one of the at least two non-posture physiological sensors does not generate signal when no touch is present between user body and the at least two non-posture physiological sensors.

15. The object for detecting a non-posture physiological function and a posture status of claim 13, wherein the non-posture physiological signals are obtained from two different areas of the body including a body side that is facing or lying down is detected.

16. The object for detecting a non-posture physiological function and a posture status of claim 13, wherein at least one of the at least two non-posture physiological sensors is a switch sensor, a tension sensor or a pressure sensor.

17. The object for detecting a non-posture physiological function and a posture status of claim 13, where the at least two non-posture physiological sensors are two electrodes that also functions as a switch or a pressure sensor to sense ECG signal, sweat, EMG signal or body fat.

18. The object for detecting a non-posture physiological function and a posture status according to claim 13, wherein one of the at least two non-posture physiological sensors is coupled to or in contact with at least one or more from a group consisting of: a switch, a tension sensor, a pressure sensor, and a pressure applicator, while the other one of the at least two non-posture physiological sensors is not coupled to or in contact with at least one or more from a group consisting of: a switch, a tension sensor, a pressure sensor, and a pressure applicator.

19. The object for detecting a non-posture physiological function and a posture status of claim 13, wherein the other one of the at least two non-posture physiological sensors is at least one of body temperature sensor, sweat wetness sensor, heartbeat sensor, plethysmography sensor, body fat analyzer, oxygen saturation sensor, EEG, respiration sensor, EMG, pulse sensor, speaking sensor, blood pressure sensor, blood glucose sensor, breathing sounds, pressure, biochemical compounds, ultrasound, urine sugar, heart sound, or lung sound sensor.

20. An object for detecting a non-posture physiological function and a posture status of a user, the object comprising:

at least two non-posture physiological sensors adapted to contact with the user's body directly or indirectly;

wherein the at least two non-posture physiological sensors sense a non-posture physiological function of the user to generate non-posture physiological signals;

a signal processor configured to determine different body position or posture of the user by generating posture characteristics from the non-posture physiological signals and referring to a judgment criteria; and wherein the non-posture physiological function of the user is used to determine the different body position or posture of the user;

wherein the object is one of a shirt, clothes, an undershirt and a coat, and has a button to connect conductive areas on both sides of a front opening of the shirt, the clothes, the undershirt or the coat.

* * * * *